(12) United States Patent
Yeung et al.

(10) Patent No.: US 9,303,020 B2
(45) Date of Patent: Apr. 5, 2016

(54) COMPOUNDS FOR THE TREATMENT OF HEPATITIS C

(71) Applicant: Bristol-Myers Squibb Company, Princeton, NJ (US)

(72) Inventors: Kap-Sun Yeung, Madison, CT (US); John F. Kadow, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 307 days.

(21) Appl. No.: 13/755,971

(22) Filed: Jan. 31, 2013

(65) Prior Publication Data
US 2013/0203775 A1  Aug. 8, 2013

Related U.S. Application Data

(60) Provisional application No. 61/596,500, filed on Feb. 8, 2012.

(51) Int. Cl.
*C07D 405/14*  (2006.01)
*C07D 405/04*  (2006.01)

(52) U.S. Cl.
CPC ............ *C07D 405/14* (2013.01); *C07D 405/04* (2013.01)

(58) Field of Classification Search
None
See application file for complete search history.

(56) References Cited

U.S. PATENT DOCUMENTS

| 7,265,152 B2 | 9/2007 | Saha et al. |
| 7,868,037 B2 | 1/2011 | Karp et al. |
| 7,994,171 B2 | 8/2011 | Yeung et al. |
| 8,048,887 B2 | 11/2011 | Yeung et al. |
| 8,198,449 B2 | 6/2012 | Pracitto et al. |
| 8,324,212 B2 | 12/2012 | Kadow et al. |
| 8,354,410 B2 | 1/2013 | Yeung et al. |
| 2009/0281336 A1 | 11/2009 | Saha et al. |

FOREIGN PATENT DOCUMENTS

| JP | 57-123181 | 7/1982 |
| WO | WO 02/16359 | 2/2002 |
| WO | WO 02/078701 | 10/2002 |
| WO | WO 2004/041201 | 5/2004 |
| WO | WO 2008/125874 | 10/2008 |
| WO | WO 2009/101022 | 8/2009 |
| WO | WO 2009/137493 | 11/2009 |
| WO | WO 2009/137500 | 11/2009 |
| WO | WO 2011/103063 | 8/2011 |
| WO | WO 2011/106929 | 9/2011 |
| WO | WO 2011/106986 | 9/2011 |
| WO | WO 2011/106992 | 9/2011 |
| WO | WO 2012/087833 | 6/2012 |

OTHER PUBLICATIONS

Database Caplus [Online], Chemical Abstracts Service, Columbus, OH, US, Grinev, A.N. et al., "Aminomethyl and aminomethyl derivatives of 5-methoxybenzofuran", Zhurnal Obshchei Khimii, 33(5):1436-1442, Coden: ZOKHA4; ISSN: 0044-460X (1963), retrieved from STN Database, Accession No. 1963:469003, RN 94004-97-4, 94623-08-2, 95220-34-1, Abstract.

Cheung, M., "The identification of pyrazolo[1,5-a]pyridines as potent p38 kinase inhibitors", Bioorganic & Medicinal Chemistry Letters, vol. 18, pp. 5428-5430 (2008).

Elsner, J. et al., "Bicyclic melatonin receptor agonists containing a ring-junction nitrogen: Synthesis, biological evaluation, and molecular modeling of the putative bioactive conformation", Bioorganic & Medicinal Chemistry, vol. 14, pp. 1949-1958 (2006).

Flint, M. et al., "Selection and Characterization of Hepatitis C Virus Replicons Dually Resistant to the Polymerase and Protease Inhibitors HCV-796 and Boceprevir (SCH 503034)", Antimicrobial Agents and Chemotherapy, vol. 53, No. 2, pp. 401-411 (2009).

Hang, J.Q. et al., "Slow Binding Inhibition and Mechanism of Resistance of Non-nucleoside Polymerase Inhibitors of Hepatitis C Virus", The Journal of Biological Chemistry, vol. 284, No. 23, pp. 15517-15529 (2009).

Kakehi, A. et al., "Preparation of New Nitrogen-Bridged Heterocycles. XIV. Further Investigation of the Desulfurization and the Rearrangement of Pyrido[1,2-d]-1,3,4-thiadiazine Intermediates", Chem. Pharm. Bull., vol. 35, No. 1, pp. 156-169 (1987).

Miki, Y. et al., "Acid-Catalyzed Reactions of 3-(Hydroxymethyl)- and 3-(1-Hydroxyethyl)pyrazolo[1,5-a]pyridines", J. Heterocyclic Chem., vol. 26, pp. 1739-1745 (1989).

Yeung, U.S. Appl. No. 61/615,971, filed Mar. 27, 2012.

*Primary Examiner* — Savitha Rao
*Assistant Examiner* — Gregg Polansky
(74) *Attorney, Agent, or Firm* — James Epperson

(57) ABSTRACT

The disclosure provides compounds of formula I, including their salts, as well as compositions and methods of using the compounds. The compounds have activity against hepatitis C virus (HCV) and may be useful in treating those infected with HCV.

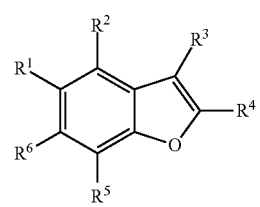

6 Claims, No Drawings

COMPOUNDS FOR THE TREATMENT OF HEPATITIS C

CROSS-REFERENCE TO RELATED APPLICATIONS

This application claims the benefit of U.S. Provisional Application Ser. No. 61/596,500 filed Feb. 8, 2012.

BACKGROUND OF THE INVENTION

The disclosure generally relates to the novel compounds of formula I, including their salts, which have activity against hepatitis C virus (HCV) and are useful in treating those infected with HCV. The disclosure also relates to compositions and methods of using these compounds.

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. *N. Engl. J. Med.* 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., *Journal of Virology* 2002, 3482-3492; and Defrancesco and Rice, *Clinics in Liver Disease* 2003, 7, 211-242.

Currently, the most effective HCV therapy employs a combination of alpha-interferon and ribavirin, leading to sustained efficacy in 40% of patients (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N. Engl. J. Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

HCV-796, an HCV NS5B inhibitor, showed an ability to reduce HCV RNA levels in patients. The viral RNA levels decreased transiently and then rebounded during dosing when treatment was with the compound as a single agent but levels dropped more robustly when combined with the standard of care which is a form of interferon and ribavirin. The development of this compound was suspended due to hepatic toxicity observed during extended dosing of the combination regimens. U.S. Pat. No. 7,265,152 and the corresponding PCT patent application WO2004/041201 describe compounds of the HCV-796 class. Other compounds have been disclosed, see for example, WO2009/101022.

The invention provides technical advantages, for example, the compounds are novel and are effective against hepatitis C. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

One aspect of the invention is a compound of formula I

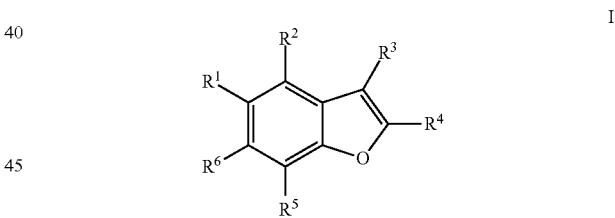

where:
$R^1$ is alkyl, cycloalkyl, alkoxy, cycloalkoxy, phenyl or pyridinyl wherein the phenyl or pyridinyl is substituted with 0-3 substituents selected from the group consisting of halo, alkyl, cycloalkyl, haloalkyl, hydroxyalkyl, alkoxyalkyl, alkoxy, cycloalkoxy, hydroxyalkyloxy, and alkoxyalkyloxy, and wherein the phenyl or pyridinyl is also substituted with 1 $CON(R^9)(R^{10})$ substituent;
$R^2$ is hydrogen, halo, alkyl, or alkoxy;
$R^3$ is imidazolyl substituted with 0-3 halo or alkyl substituents;
$R^4$ is phenyl that is independently substituted with 0-2 halo, alkyl, or alkoxy or is para substituted with $X$—$Ar^1$;
$R^5$ and $R^6$ are independently hydrogen, nitro, halo, alkyl, alkoxy, $N(R^7)(R^8)$, or alkylsulfonyl;
$R^7$ and $R^8$ are independently hydrogen, alkyl, cyanoalkyl, haloalkyl, (cycloalkyl)alkyl, cycloalkyl, hydroxyalkyl, alkoxyalkyl, alkylcarbonyl, alkoxycarbonyl, haloalkoxycarbonyl, alkylsulfonyl, alkylsulfonylalkyl, $SO_2N(R^{13})(R^{14})$, or benzyl where said benzyl is substituted with 0-3 substituents selected from halo, alkyl, haloalkyl, alkoxy, haloalkoxy, carboxy, and alkoxycarbonyl;

or $N(R^7)(R^8)$ taken together is azetidinyl, pyrrolidinyl, piperidinyl, or piperazinyl, and is substituted with 0-2 substituents selected from alkyl, hydroxyalkyl, or hydroxy;

$R^9$ is alkyl, haloalkyl, cycloalkyl, (alkyl)cycloalkyl, (haloalkyl)cycloalkyl, (cycloalkyl)cycloalkyl, adamantyl, or

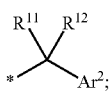

$R^{10}$ is hydrogen;
$R^{11}$ is hydrogen, alkyl, hydroxyalkyl, or alkoxyalkyl;
$R^{12}$ is hydrogen, alkyl, hydroxyalkyl, or alkoxyalkyl;
or $R^{11}$ and $R^{12}$ taken together is ethylene, propylene, butylenes, or pentylene substituted with 0-2 halo or alkoxy;
or $R^{11}$ and $R^{12}$ taken together is —CH$_2$OCH$_2$—, —OCH$_2$CH$_2$—, —CH$_2$OCH$_2$CH$_2$—, —OCH$_2$CH$_2$CH$_2$—, —OCH$_2$CH$_2$CH$_2$CH$_2$—, —CH$_2$OCH$_2$CH$_2$CH$_2$—, or —CH$_2$CH$_2$OCH$_2$CH$_2$—;
$R^{13}$ is hydrogen or alkyl;
$R^{14}$ is hydrogen or alkyl;
X is —O— or —NH—;
$Ar^1$ is phenyl or para-halophenyl; and
$Ar^3$ is phenyl, pyridinyl, pyrazinyl, pyrimidinyl, pyrazolyl, isoxazolyl, imidazolyl, oxazolyl, thiazolyl, oxadiazolyl, oxadiathiazolyl, triazolyl, or tetrazolyl, and is substituted with 0-3 substituents selected from halo, alkyl, or dialkylamino;
or a pharmaceutically acceptable salt thereof.

Another aspect of the invention is a compound of formula I where $R^1$ is phenyl substituted with 0-3 substituents selected from the group consisting of halo and alkoxy, and is also substituted with 1 $CON(R^9)(R^{10})$ substituent;
$R^2$ is hydrogen or halo;
$R^3$ is imidazol-2-yl substituted with 0-3 halo or alkyl substituents;
$R^4$ is phenyl that is para substituted with halo;
$R^5$ is hydrogen
$R^6$ is hydrogen, nitro, halo, alkyl, alkoxy, $N(R^7)(R^8)$, or alkylsulfonyl;
$R^9$ is alkyl or

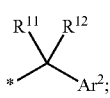

$R^{10}$ is hydrogen; and
$Ar^2$ is phenyl, pyridinyl, or pyrimidinyl, and is substituted with 0-3 substituents selected from halo or alkyl;
or a pharmaceutically acceptable salt thereof.

Another aspect of the invention is a compound of formula I wherein $R^1$ is phenyl substituted with 2 substituents selected from the group consisting of halo, alkyl, and alkoxy, and is also substituted with 1 $CON(R^9)(R^{10})$ substituent; $R^2$ is halo; $R^3$ is imidazol-2-yl; $R^4$ is phenyl that is para substituted with halo; $R^5$ is hydrogen; $R^6$ is hydrogen; $R^9$ is

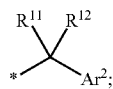

$R^{10}$ is hydrogen; $R^{11}$ and $R^{12}$ taken together is ethylene; and $Ar^2$ is pyrimidinyl; or a pharmaceutically acceptable salt thereof.

Another aspect of the invention is a compound of formula I where $R^1$ is alkyl, cycloalkyl, alkoxy, cycloalkoxy, phenyl or pyridinyl wherein the phenyl or pyridinyl is substituted with 0-3 substituents selected from the group consisting of halo, alkyl, cycloalkyl, haloalkyl, hydroxyalkyl, alkoxyalkyl, alkoxy, cycloalkoxy, hydroxyalkyloxy, and alkoxyalkyloxy, and wherein the phenyl or pyridinyl is also substituted with 1 $CON(R^9)(R^{10})$ substituent.

Another aspect of the invention is a compound of formula I where $R^1$ is phenyl or pyridinyl wherein the phenyl or pyridinyl is substituted with 0-3 substituents selected from the group consisting of halo, alkyl, cycloalkyl, haloalkyl, hydroxyalkyl, alkoxyalkyl, alkoxy, cycloalkoxy, hydroxyalkyloxy, and alkoxyalkyloxy, and is also substituted with 1 $CON(R^9)(R^{10})$ substituent.

Another aspect of the invention is a compound of formula I where $R^2$ is hydrogen, halo, alkyl, or alkoxy.

Another aspect of the invention is a compound of formula I where $R^2$ is hydrogen or halo.

Another aspect of the invention is a compound of formula I where $R^3$ is imidazolyl substituted with 0-3 halo or alkyl substituents.

Another aspect of the invention is a compound of formula I where $R^3$ is imidazolyl.

Another aspect of the invention is a compound of formula I where $R^3$ is imidazol-2-yl.

Another aspect of the invention is a compound of formula I where $R^4$ is phenyl that is independently substituted with 0-2 halo, alkyl, or alkoxy substituents or is para substituted with X—$Ar^1$.

Another aspect of the invention is a compound of formula I where $R^4$ is phenyl that is substituted with 0-1 halo substituent.

Another aspect of the invention is a compound of formula I where $R^5$ and $R^6$ are independently hydrogen, nitro, halo, alkyl, alkoxy, $N(R^7)(R^8)$, or alkylsulfonyl.

Another aspect of the invention is a compound of formula I where $R^5$ is hydrogen and $R^6$ is hydrogen or $N(R^7)(R^8)$.

Another aspect of the invention is a compound of formula I where $R^7$ and $R^8$ are independently hydrogen, alkyl, cyanoalkyl, haloalkyl, (cycloalkyl)alkyl, cycloalkyl, hydroxyalkyl, alkoxyalkyl, alkylcarbonyl, alkoxycarbonyl, haloalkoxycarbonyl, alkylsulfonyl, alkylsulfonylalkyl, $SO_2N(R^{13})(R^{14})$, or benzyl where said benzyl is substituted with 0-3 substituents selected from halo, alkyl, haloalkyl, alkoxy, haloalkoxy, carboxy, and alkoxycarbonyl.

Another aspect of the invention is a compound of formula I where $N(R^7)(R^8)$ taken together is azetidinyl, pyrrolidinyl, piperidinyl, or piperazinyl, and is substituted with 0-2 substituents selected from alkyl, hydroxyalkyl, or hydroxyl.

Another aspect of the invention is a compound of formula I where $R^9$ is alkyl, haloalkyl, cycloalkyl, (alkyl)cycloalkyl, (haloalkyl)cycloalkyl, (cycloalkyl)cycloalkyl, adamantyl, or

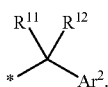

Another aspect of the invention is a compound of formula I where $R^{10}$ is hydrogen.

Another aspect of the invention is a compound of formula I where $R^9$ is alkyl or

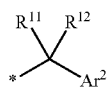

and $R^{10}$ is hydrogen.

Another aspect of the invention is a compound of formula I where $R^{11}$ is hydrogen, alkyl, hydroxyalkyl, or alkoxyalkyl.

Another aspect of the invention is a compound of formula I where $R^{11}$ is alkyl.

Another aspect of the invention is a compound of formula I where $R^{12}$ is hydrogen, alkyl, hydroxyalkyl, or alkoxyalkyl.

Another aspect of the invention is a compound of formula I where $R^{12}$ is alkyl.

Another aspect of the invention is a compound of formula I where $R^{11}$ and $R^{12}$ taken together is ethylene, propylene, butylene, or pentylene substituted with 0-2 halo or alkoxy.

Another aspect of the invention is a compound of formula I where $R^{11}$ and $R^{12}$ taken together is ethylene, propylene, butylene, or pentylene.

Another aspect of the invention is a compound of formula I where $R^{11}$ and $R^{12}$ taken together is ethylene.

Another aspect of the invention is a compound of formula I where $R^{11}$ is alkyl; $R^{12}$ is alkyl; or $R^{11}$ and $R^{12}$ taken together is ethylene, propylene, butylene, or pentylene; or a pharmaceutically acceptable salt thereof.

Another aspect of the invention is a compound of formula I where or $R^{11}$ and $R^{12}$ taken together is —CH$_2$OCH$_2$—, —OCH$_2$CH$_2$—, —CH$_2$OCH$_2$CH$_2$—, —OCH$_2$CH$_2$CH$_2$—, —OCH$_2$CH$_2$CH$_2$CH$_2$—, —CH$_2$OCH$_2$CH$_2$CH$_2$—, or —CH$_2$CH$_2$OCH$_2$CH$_2$—.

Another aspect of the invention is a compound of formula I where or $R^{11}$ and $R^{12}$ taken together is —CH$_2$OCH$_2$—.

Another aspect of the invention is a compound of formula I where $R^{13}$ is hydrogen or alkyl.

Another aspect of the invention is a compound of formula I where $R^{14}$ is hydrogen or alkyl.

Another aspect of the invention is a compound of formula I where X is —O— or —NH—.

Another aspect of the invention is a compound of formula I where X is —O—.

Another aspect of the invention is a compound of formula I where Ar$^1$ is phenyl or para-halophenyl.

Another aspect of the invention is a compound of formula I where Ar$^2$ is phenyl, pyridinyl, pyrazinyl, pyrimidinyl, pyrazolyl, isoxazolyl, imidazolyl, oxazolyl, thiazolyl, oxadiazolyl, oxadiathiazolyl, triazolyl, or tetrazolyl, and is substituted with 0-3 substituents selected from halo, alkyl, or dialkylamino;

Another aspect of the invention is a compound of formula I where Ar$^2$ is phenyl, pyridinyl, pyrazinyl, or pyrimidinyl; or a pharmaceutically acceptable salt thereof.

Any scope of any variable, including $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, X, Ar$^1$, or Ar$^2$ can be used independently with the scope of any other instance of a variable.

Unless specified otherwise, these terms have the following meanings. "Halo" means fluoro, chloro, bromo, or iodo. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Halo" includes all halogenated isomers from monohalo substituted to perhalo substituted in substituents defined with halo, for example, "Haloalkyl" and "haloalkoxy", "halophenyl", "halophenoxy." Ethylene means ethanediyl or —CH$_2$CH$_2$—; propylene means propanediyl or —CH$_2$CH$_2$CH$_2$—; butylene means butanediyl or —CH$_2$CH$_2$CH$_2$CH$_2$—; pentylene means pentanediyl or —CH$_2$CH$_2$CH$_2$CH$_2$CH$_2$—. "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a four- to six-membered aromatic or non-aromatic carbocyclic ring. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Parenthetic and multiparenthetic terms are intended to clarify bonding relationships to those skilled in the art. For example, a term such as ((R)alkyl) means an alkyl substituent further substituted with the substituent R. Substituents which are illustrated by chemical drawing to bond at variable positions on a multiple ring system (for example a bicyclic ring system) are intended to bond to the ring where they are drawn to append. For example, substituents $R^1$ and $R^2$ of formula IV are intended to bond to the benzene ring of formula IV and not to the thiophene ring.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, camsylate, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms. The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Pharmaceutical Compositions and Methods of Treatment

The compounds demonstrate activity against HCV NS5B and can be useful in treating HCV and HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon or a ribavirin. Another aspect of the invention is where the interferon is selected from interferon alpha 2B, pegylated interferon alpha, consensus interferon, interferon alpha 2A, interferon lambda, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophosphate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound or a pharmaceutically acceptable salt thereof.

Another aspect of the invention is a method of inhibiting the function of the HCV NS5B protein comprising contacting the HCV NS5B protein with a compound or a pharmaceutically acceptable salt thereof.

Another aspect of the invention is a method of treating an HCV infection in a patient comprising administering to the patient a therapeutically effective amount of a compound or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon or a ribavirin.

Another aspect of the invention is the method where the interferon is selected from interferon alpha 2B, pegylated interferon alpha, consensus interferon, interferon alpha 2A, interferon lambda, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophosphate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 1.

TABLE 1

| Brand Name | Physiological Class | Type of Inhibitor or Target | Source Company |
| --- | --- | --- | --- |
| NIM811 | | Cyclophilin Inhibitor | Novartis |
| Zadaxin | | Immuno-modulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/ Viropharma |
| NM-283 | Antiviral | NS5B Replicase Inhibitor | Idenix/Novartis |
| GL-59728 | Antiviral | NS5B Replicase Inhibitor | Gene Labs/ Novartis |
| GL-60667 | Antiviral | NS5B Replicase Inhibitor | Gene Labs/ Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |

TABLE 1-continued

| Brand Name | Physiological Class | Type of Inhibitor or Target | Source Company |
|---|---|---|---|
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immuno-suppressant | F. Hoffmann-La Roche LTD, Basel, Switzerland |
| Civacir | Immunosuppressant | HCV IgG immuno-suppressant | Nabi Biopharmaceuticals Inc., Boca Raton, FL |
| Albuferon-α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/ Valentis |
| Wellferon | Interferon | Lympho-blastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |

TABLE 1-continued

| Brand Name | Physiological Class | Type of Inhibitor or Target | Source Company |
|---|---|---|---|
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| Boceprevir | Antiviral | serine protease inhibitor | Schering Plough |
| TMS-435 | Antiviral | serine protease inhibitor | Tibotec BVBA, Mechelen, Belgium |
| BI-201335 | Antiviral | serine protease inhibitor | Boehringer Ingelheim Pharma KG, Ingelheim, Germany |
| MK-7009 | Antiviral | serine protease inhibitor | Merck |
| PF-00868554 | Antiviral | replicase inhibitor | Pfizer |
| ANA598 | Antiviral | Non-Nucleoside NS5B Polymerase Inhibitor | Anadys Pharmaceuticals, Inc., San Diego, CA, USA |
| IDX375 | Antiviral | Non-Nucleoside Replicase Inhibitor | Idenix Pharmaceuticals, Cambridge, MA, USA |
| BILB 1941 | Antiviral | NS5B Polymerase Inhibitor | Boehringer Ingelheim Canada Ltd R&D, Laval, QC, Canada |
| PSI-7851 | Antiviral | Nucleoside Polymerase Inhibitor | Pharmasset, Princeton, NJ, USA |
| PSI-7977 | Antiviral | Nucleotide NS5B Polymerase Inhibitor | Pharmasset, Princeton, NJ, USA |
| VCH-759 | Antiviral | NS5B Polymerase Inhibitor | ViroChem Pharma |
| VCH-916 | Antiviral | NS5B Polymerase Inhibitor | ViroChem Pharma |
| GS-9190 | Antiviral | NS5B Polymerase Inhibitor | Gilead |
| Peg-interferon lamda | Antiviral | Interferon | ZymoGenetics/Bristol-Myers Squibb |

Synthetic Methods

The compounds may be made by methods known in the art including those described below. Some reagents and intermediates are known in the art. Other reagents and intermediates can be made by methods known in the art using commercially available materials. The variables (e.g. numbered "R" substituents) used to describe the synthesis of the compounds are intended only to illustrate how to make and are not to be confused with variables used in the claims or in other sections of the specification. Abbreviations used within the schemes generally follow conventions used in the art.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "4" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

A route to prepare Compound 1 is shown in Scheme 1.

Scheme 1.

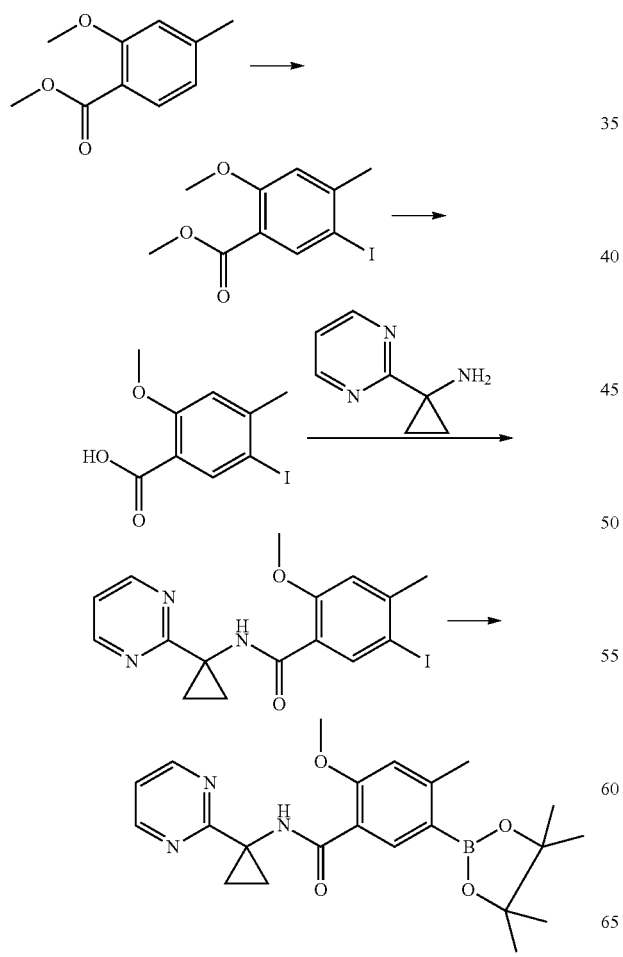

Scheme 2.

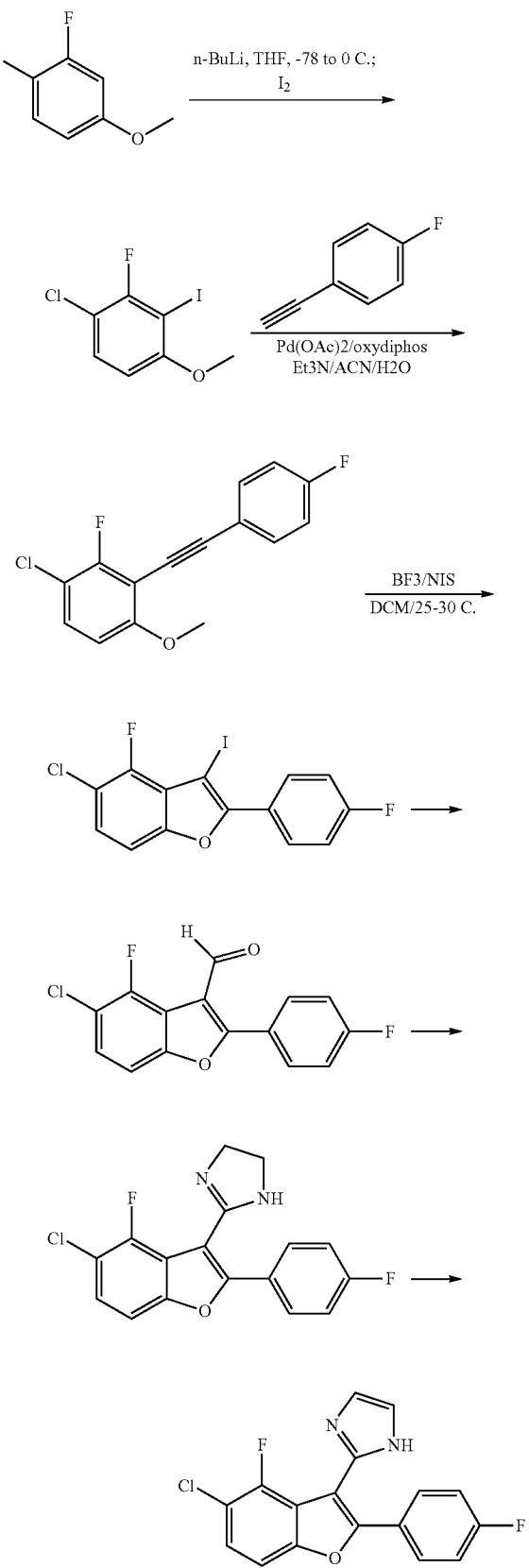

Scheme 3.

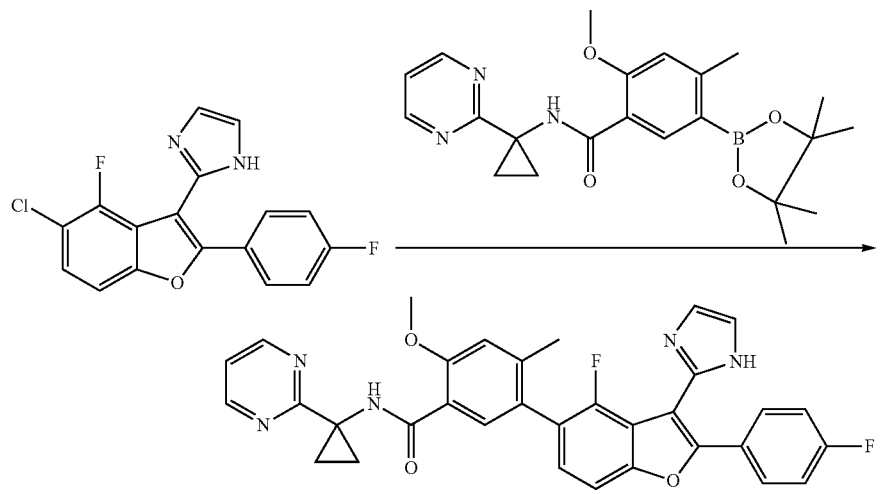

Example 1

Preparation of methyl 5-iodo-2-methoxy-4-methylbenzoate. To a solution of methyl 2-methoxy-4-methylbenzoate (2.6 g, 14.43 mmol) in methanol (25 ml) at room temperature in a 100 ml round bottomed (RB) flask was added iodine monochloride (3.62 ml, 72.1 mmol) in methanol dropwise. The reaction mixture was heated at 50° C. for 15 hours. The methanol was concentrated, diluted with water and extracted with ethyl acetate (3×25 ml). The combined organic extracts were washed with 0.1N HCl, water and brine solution. The organic layer was dried over $Na_2SO_4$, filtered and concentrated. The crude material was used for the next step without further purification (3.2 g, 73%). LCMS: (ES+) m/z=307 $(M+H)^+$; Column: ZORBAX SB C18 (4.6×50) mm, 5 μm; Moblie (M) phase A: 10% MeOH-90% $H_2O$-0.1% TFA; Moblie (M) phase B: 90% MeOH-10% $H_2O$-0.1% TFA; Flow: 5 ml/min; Time (min.): 0 2 3; % B: 0 100 0; Retention Time (RT): 1.87 min.

Preparation of 5-iodo-2-methoxy-4-methylbenzoic acid. To a mixture of methyl 5-iodo-2-methoxy-4-methylbenzoate (3.0 g, 9.80 mmol) in ethanol (10 ml) in a 50 ml RB flask was added an aqueous solution of NaOH (0.784 g, 19.60 mmol, 1M). The reaction mixture was stirred at room temperature overnight. The solvent was removed under vacuum, the solid filtered and dried to give the titled compound (2.2 g, 74%). LCMS: (ES+) m/z=292 $(M+H)^+$; Column. PUROSPHER@star RP-18 (4×55) mm, 3 μm; Buffer: 20 mM $NH_4OAc$ IN WATER; Mphase A: Buffer+MeCN (90+10); Mphase B: Buffer+MeCN (10+90); Flow: 2.5 ml/min Time (min.): 0 2 2.5 3; % B: 0 100 100 0; RT: 1.04 min.

Preparation of 5-iodo-2-methoxy-4-methyl-N-(1-(pyrimidin-2-yl)cyclopropyl)benzamide. A mixture of 1-(pyrimidin-2-yl)cyclopropanamine (2.00 g, 14.8 mmol) and 5-iodo-2-methoxy-4-methylbenzoic acid (4.75 g, 16.28 mmol) in DMF (8 ml) in a 25 ml RB flask was cooled to 0° C., and then added with N,N-diisopropylethylamine (12.92 ml, 74.0 mmol) followed by HATU (6.75 g, 17.76 mmol). The reaction mixture was stirred at room temperature overnight. The reaction mixture was added ice water and extracted with ethyl acetate (3×25 ml). The combined organic extracts were washed with brine solution, dried over $Na_2SO_4$, filtered and concentrated. The crude product was purified by using a silica gel (60-120 mesh) column with 60% ethyl acetate in hexane as an eluent. Yield: 3.2 g, 48%. $^1H$ NMR (400 MHz, $CDCl_3$): δ 8.57 (d, J=4.8 Hz, 2H), 8.52 (s, 1H), 8.47 (s, 1H), 7.03 (t, 1H, J=5.0 Hz), 4.02 (s, 3H), 2.63 (s, 3H), 1.83-1.80 (m, 2H), 1.52-1.49 (m, 2H). LCMS: (ES+) m/z=410 $(M+H)^+$; Column—Ascentis Express C8 (5×2.1 mm-2.7 μm); Mphase A: 2% MeCN-98% $H_2O$-10 mM $NH_4COOH$; Mphase B: 98% MeCN-2% $H_2O$-10 mM $NH_4COOH$; Flow=1 ML/MIN; Time: 0.0, 1.5, 3.2; % A: 100.0, 0.0, 0.0; % B: 0.0, 100.0, 100.0; RT: 1.904 min.

Preparation of 2-methoxy-4-methyl-N-(1-(pyrimidin-2-yl)cyclopropyl)-5-(4,4,5,5-tetramethyl-1,3,2-dioxaborolan-2-yl)benzamide. To a mixture of 5-iodo-2-methoxy-4-methyl-N-(1-(pyrimidin-2-yl)cyclo-propyl)benzamide (1.6 g, 3.91 mmol) in dioxane (10 ml) in a 50 ml RB flask was added bis(pinacolato)diboron (1.191 g, 4.69 mmol) and potassium acetate (1.151 g, 11.73 mmol). The mixture was degassed for 10 min, added $PdCl_2$(dppf) (0.286 g, 0.391 mmol) and degassed again for 10 minutes. The reaction mixture was then heated at 100° C. overnight. The solvent was removed and the residue filtered through a Celite bed with washing using ethyl acetate. The ethyl acetate solution was then washed with water, dried over $Na_2SO_4$, filtered and concentrated. The crude product was purified by preparative-HPLC. LCMS: (ES+) m/z=$(M+H)^+$; Column. PUROSPHER@star RP-18 (4×55) mm, 3 μm; Buffer: 20 mM$NH_4OAC$ IN WATER; Mphase A: Buffer+MeCN (90+10); Mphase B: Buffer+MeCN (10+90); Flow: 2.5 ml/min; Time (min.): 0 2 2.5 3; % B: 0 100 100 0; RT: 1.90 min.

Preparation of 5-chloro-4-fluoro-2-(4-fluorophenyl)benzofuran-3-carbaldehyde. To a mixture of 5-chloro-4-fluoro-2-(4-fluorophenyl)-3-iodobenzofuran (2.0 g, 5.12 mmol) in THF (15 ml) under a $N_2$ atmosphere in a 50 ml two necked RB flask cooled to 78° C. was added n-butyllithium (0.328 g, 5.12 mmol) slowly, and the mixture stirred at the same temperature for 1 hour. 1-Piperidinecarboxaldehyde (5.79 g, 51.2 mmol) was then added and the mixture was maintained stirring at the same temperature for 3 hours. The reaction mixture was quenched with 1N HCl and extracted with diethyl ether (3×25 ml). The combined organic extracts were dried over $Na_2SO_4$, filtered and concentrated to give the titled compound (1.2 g, 74%). $^1H$ NMR (400 MHz, $CDCl_3$): δ 10.39 (d, J=2.4 Hz, 1H), 8.18-8.14 (m, 2H), 7.44-7.40 (m, 1H), 7.33 (d, J=9.2, 1H), 7.27-7.23 (m, 2H).

Preparation of 2-(5-chloro-4-fluoro-2-(4-fluorophenyl) benzofuran-3-yl)-4,5-dihydro-1H-imidazole. A mixture of 5-chloro-4-fluoro-2-(4-fluorophenyl)benzofuran-3-carbaldehyde (1.2 g, 4.10 mmol) and ethylenediamine (0.277 m, 4.10 mmol) in t-BuOH (15 ml) under a $N_2$ atmosphere in a 50 ml RB flask was stirred at room temperature for 30 minutes. Potassium carbonate (0.567 g, 4.10 mmol) followed by iodine (1.041 g, 4.10 mmol) were then added and the reaction mixture was heated at 70° C. for 2 hours. The solvent was removed and the residue diluted with ethyl acetate. The mixture was washed with 10% sodium thiosulfate solution. The organic layer was dried over $Na_2SO_4$, filtered and concentrated. The crude product was purified by using combiflash silica column using 8% methanol in chloroform as an eluent. The desired fractions were collected and concentrated to give the titled product (0.7 g, 52%). $^1$H NMR (400 MHz, $CDCl_3$): δ 7.77-7.75 (m, 2H), 7.37-7.34 (m, 1H), 7.27-7.16 (m, 3H), 3.90 (s, 4H).

Preparation of 2-(5-chloro-4-fluoro-2-(4-fluorophenyl) benzofuran-3-yl)-1H-imidazole. To a mixture of 2-(5-chloro-4-fluoro-2-(4-fluorophenyl)benzofuran-3-yl)-4,5-dihydro-1H-imidazole (0.65 g, 1.954 mmol) in DMSO (5 ml) in a 25 ml RB flask was added potassium carbonate (0.405 g, 2.93 mmol) and iodobenzene diacetate (0.755 g, 2.344 mmol). The reaction mixture was stirred at room temperature in darkness overnight. The reaction mixture was added water and extracted with ethyl acetate (3×25 ml). The combined organic extracts were dried over $Na_2SO_4$, filtered and concentrated. The crude product was purified by using 40 g combiflash silica column with 11% methanol in chloroform as an eluent. The desired fractions were collected and concentrated to give the titled product (0.25 g, 39%). $^1$H NMR (400 MHz, $CDCl_3$): δ 9.45 (s, 1H), 7.92-7.89 (m, 2H), 7.36-7.30 (m, 2H), 7.26-7.21 (m, 2H), 7.11-7.07 (m, 2H).

Preparation of 5-(4-fluoro-2-(4-fluorophenyl)-3-(1H-imidazol-2-yl)benzofuran-5-yl)-2-methoxy-4-methyl-N-(1-(pyrimidin-2-yl)cyclopropyl)benzamide with palladium (II) acetate (6.79 mg, 0.030 mmol) followed by 2-(dicyclohexyl-phosphino)-2',4',6'-triisopropylbiphenyl (0.144 g, 0.302 mmol) under a $N_2$ atmosphere. The resulting mixture was again degassed for 5 minutes. The reaction mixture was then heated at 90° C. The reaction mixture was diluted with ethyl acetate, washed with water, dried over $Na_2SO_4$, filtered and concentrated. The crude product was purified by using 40 g combiflash silica column with 6% methanol in chloroform as an eluent. The desired fractions were collected and concentrated to give the titled product (8 mg, Yield: 4.6%). $^1$H NMR (400 MHz, $CD_3OD$): δ 8.65 (d, J=4.8, 2H), 7.88 (s, 1H), 7.69-7.65 (m, 2H), 7.56 (d, J=8.4, 1H), 7.31-7.27 (m, 3H), 7.24-7.16 (m, 4H), 4.08 (s, 3H), 2.28 (s, 3H), 1.81-1.78 (m, 2H), 1.52-1.49 (m, 2H). $^{19}$F NMR (376.6 MHz, DMSO-$d_6$) −113.33, −124.62. LCMS: (ES+) m/z=578.2 (M+H)$^+$; Column—Ascentis Express C8 (5×2.1 mm-2.7 µm); Mphase A: 2% MeCN-98% $H_2O$-10 mM $NH_4COOH$; Mphase B: 98% MeCN-2% H20-10 mM $NH_4COOH$; Flow=1 ML/MIN;

| Time | % A | % B |
|---|---|---|
| 0.0 | 100.0 | 0.0 |
| 1.5 | 0.0 | 100.0 |
| 3.2 | 0.0 | 100.0 |

RT: 1.96 min wavelengths: 220 nm

Preparation of 1-chloro-2-fluoro-3-iodo-4-methoxybenzene. Charged Tetrahydrofuran (8.35 L) into a 3-L four-neck flask equipped with a mechanical stirrer, an addition funnel and a temperature probe under N2 atmosphere. Charged 4-Chloro-3-fluoroanisole (1000 g) to a 3-L four-neck flask equipped with a mechanical stirrer, an addition funnel and a temperature probe. Cooled the reaction mass to −60° C. to −70° C. Added n-Butyl Lithium in hexanes (30%, 1.42 kg) in to reaction mass through canula under nitrogen atmosphere slowly, while maintaining the temperature of the reaction

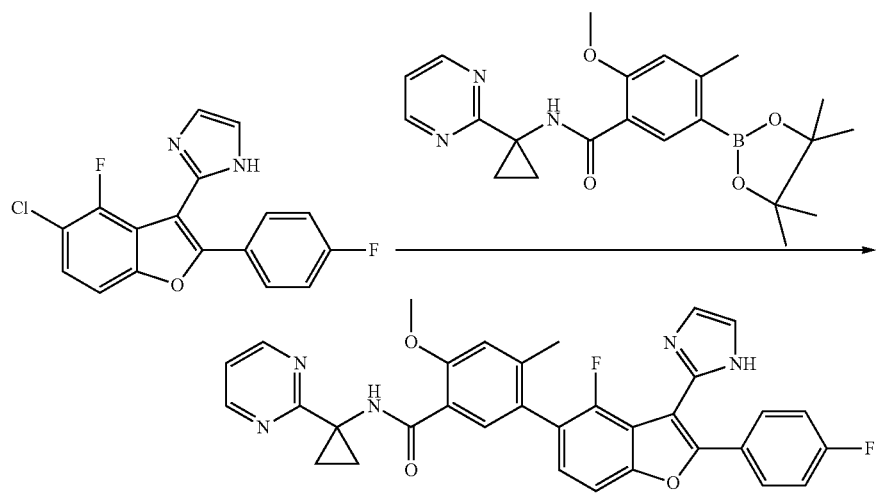

To a mixture of 2-(5-chloro-4-fluoro-2-(4-fluorophenyl) benzofuran-3-yl)-1H-imidazole (0.1 g, 0.302 mmol) and 2-methoxy-4-methyl-N-(1-(pyrimidin-2-yl)cyclopropyl)-5-(4,4,5,5-tetramethyl-1,3,2-dioxaborolan-2-yl)benzamide (0.186 g, 0.454 mmol) in dioxane (2 ml) in a sealed tube was added water (0.1 ml) and sodium carbonate (0.080 g, 0.756 mmol). The resulting mixture was degassed for 10 min, added mass below −60° C. Maintained the reaction at below −60° C. for 2 h. Meanwhile Iodine solution prepared by dissolving Iodine (2.405 kg) in Tetrahydrofuran (2.4 L) at 25-28° C. Transferred the Iodine solution in step #6 into a clean addition funnel with THF (500 mL) rinse. Added Iodine solution from the addition funnel to the reaction over 120 min while maintaining the internal temperature at <−60° C. Removed cooling bath and allowed to attain −5° C. to 0° C. Submitted the IPC sample when it reaches −5° C. to 0° C.[1]. A sample was removed at ~2 h and checked by HPLC-97.06 AP; Int-01-0.59 AP. Work Up: Quenched the reaction with 20% Na2SO2O3 solution (1.015 kg of sodium thiosulphate dissolved in 5.1 L of DM water) while maintaining the internal temperature at <10° C. Allowed RM to warm to RT. Transfer resulting biphasic mixture into separating funnel, rinse the flask with THF (1.2 L; 1.0-1.5 Vol wrt Int-1), and transfer to separating flask. Removed and retain bottom aqueous phase for further extraction. Concentrated the organic layer. Dissolved concentrated mass in EtOAc (8.0 L; 8.0-8.5 Vol wrt Int-1) Extract the retained aqueous phase with EtOAc (7.1 L: 7.0-7.5 Vol wrt Int-1). Combined all organic phases, Rinse the flask with EtOAc (1.0 L; 1.0-1.5 Vol wrt Int-1). Washed organic phases with DM water (5.7 L; 5.0-6.0 Vol wrt Int-1). Concentrated the organic layer[2] on rotovap at 45-50° C. completely. Purification: Added Acetonitrile (5.1 L; 5.0-5.5 vol wrt Int-01). Warmed to 55° C. to dissolve all solid. Rotate the above mass in rotavapor flask at 55° C. for 10 min. Cooled to ambient temperature. Transferred the mass into a clean reactor, rinse the flask with Acetonitrile (1.0 L; 1.0-1.2 vol wrt Int 01) and add rinse into reactor. Added water (1 L; 1.0-1.2 vol wrt Int-01) in to reactor with stirring. Stirred the resulting slurry for 15 min. Added water (5.3 L; 5.0-5.5 Vol wrt Int-01) over 15 min. Stirred the above mass at ambient temperature for 15 min. Unload the mass into a container, rinsed the reactor with water (1 L; 1.0-1.2 vol wrt Int-01), and collected the rinse in same container. Filtered the solid. Rinsed the container with water (1 L; 1.0-1.2 vol wrt Int-01), filtered the rinse. Washed filter cake with water (3.3 L; 3.0-3.5 Vol wrt Int-01). Suck dried for 2 h, then dried at 55° C. in VTD for 15 h. Unload the material. (LOD should be less than 1%). Wt: 1533 g (85.9% yield). Description (color and appearance): Off White crystalline solid. HPLC RT Time 4.897 min Under following conditions: Detector: 210 nm; Injection volume 5.00 µL; Run Time 15 min; Column. YMC UltraHT Pro C18 (50 mm×3.0 mm), 2.0µ; Mobile Phase A—0.05% TFA in MillQ Water; Mobile Phase B—0.05% TFA in Acetonitrile; Flow: 1.0 mL/min; Column Oven—40° C.; Time (min)—0 05 10 12 15; B Conc.—10 90 90 10 10. NMR: ($^1$H NMR, 400 MHz, dmso-d6) δ 7.58 (t, 8.8 Hz, 1H), 6.89 (m, 1H), 3.87 (s, 3H).

Preparation of 1-chloro-2-fluoro-3-((4-fluorophenyl)ethynyl)-4-methoxybenzene. Acetonitrile (31.5 L; 12.5 vol wrt Int-2) in to the reactor under nitrogen atmosphere at ambient temperature. Charged chlorofluoroiodomethoxybenzene (2.5 kg.) into the reactor with stirring. Charged DM water (12.5 L; 5-5.5 Vol wrt Int-2). Charged TEA (1.6 kg; 1.8 eq wrt Int-2) Purged N2 for NLT 60 min. Charged Oxydiphos (0.24 kg; 5 mol % wrt Int-2), Charged Palladium acetate (49 g; 2.5 mol % wrt Int-2), Charged 4-Fluoro phenylacetylene (1.58 kg; 1.5 eq wrt Int-2) with continuous purging of nitrogen[1]. Continued N2 Purging for NLT 10 min. Raised the temperature to 70-80° C. Stirred the reaction at 70-80° C. for 5 hrs. Reaction progress was monitored by HPLC. Work Up: After completion of the reaction, cooled the reaction mass to 25-30° C. Charged Ethylacetate (7.75 L; 3-3.5 Vol wrt Int-02), stirred for 5 min. Added DM water (4 L; 1.5-1.6 vol wrt Int-02), stirred for 5 min. Removed and retained bottom aqueous phase for further extraction. Remove and retained top organic phase for further wash. Extract the retained aqueous phase with EtOAc (13.4 L, 5-5.5 Vol wrt Int-02). Combined all organic phases and washed with water (8 L; 3-3.5 Vol). Concentrated the organic phases[2] on rotovap at 45° C. completely. Purification: Dissolved crude product in MTBE (25 L; 10-1.5 Vol wrt Int-02) at 45 C. Cooled the mass to ambient temperature. Unloaded the reaction mass, rinse the reactor with MTBE (2.5 L; 1.0-1.5 Vol wrt Int-2). Filtered through celite bed, rinse the container with MTBE (2.5 L; 1.0-1.5 Vol wrt Int-2) and filter the rinse. Washed filter bed with MTBE (5.0 L, 2.0-2.5 Vol wrt Int-2). Concentrated under vacuum at 40° C. to 2-3 Vol stage (wrt Int-2). Charged Methanol (17.53 L; 7.0-7.5 Vol wrt Int-02). Concentrate to 2-3 vol stage[3] (wrt Int-2). Cooled to 0° C. Filtered the solid. Washed solid with chilled methanol (0° C.) (12.5 L; 5-5.5 Vol wrt Int-02). Suck dried for 1 hr, and then dried in VTD for 5 hr. at 50-55° C. Wt: 1800 g (74.1% yield). Description (color and appearance): Brown crystalline solid. Purity by HPLC (%): 99%; HPLC RT Time 5.656 min under following conditions: Detector: 210 nm; Injection volume 5.00 µL; Run Time 15 min; Column: YMC UltraHT Pro C18 (50 mm×3.0 mm), 2.0µ; Mobile Phase A—0.05% TFA in MillQ Water; Mobile Phase B—0.05% TFA in Acetonitrile; Flow: 1.0 mL/min; Column Oven—40° C.; Time (min)—0 05 10 12 15; B Conc.—10 90 90 10 10. NMR: ($^1$H NMR, 400 MHz, dmso-d$_6$) δ 7.57 (m, 3H), 7.29 (t, 8.8 Hz, 2H), 7.00 (d, 9.2 Hz, 1H).

Preparation of 5-chloro-4-fluoro-2-(4-fluorophenyl)-3-iodobenzofuran. Charged DCM (30 L; 10 Vol wrt the diphenylacetylene made above) into the reactor under N$_2$ atmosphere at ambient temperature. Charged the diphenylacetylene (3 kg; 1 eq) in to reactor with stirring. Charged NIS (3.6 kg; 1.5 eq wrt the diphenylacetylene) at ambient temperature. Stirred the reaction mass for 5 min. Cooled the reaction to 15-20° C. Charged Borontrifluoride diethyletherate (3.5 kg; 1.2 eq wrt Int-03) slowly at below 30° C. Stirred the reaction at ambient temperature for 1 hr[1]. Reaction progress was monitored by HPLC. IPC-1 hr-95.17 AP; Int-03-ND. Work Up: After completion of the reaction, cooled the reaction mass to 10-15° C. Added 20% Sodium bisulphite solution (10 Vol wrt Int-03, 6 kg dissolved in 30 L of DM water) at below 30° C. Stirred for 10-15 min. Filtered the reaction mass through celite bed, rinse the reactor with 3.0 L of DCM (1.0-1.5 Vol wrt Int-3), filter the rinse. Washed filter bed with DCM (6 L, 2.0-2.5 Vol wrt Int-03). Separated the two layers from filtrate. Extract the aqueous layer with DCM (9 L, 3 Vol wrt Int-03). Combined all organic layers. Washed organic layer with DM water (15 L*2 times; 10 Vol wrt Int-03). Concentrated the organic layer[2] completely on rotavapor under vacuum at 35-40° C. Purification: Dissolved the concentrated mass in MTBE (36 L; 12.0-12.5 Vol wrt Int-03) at 40° C. and then cooled to ambient temperature. Unloaded the mass, rinsed reactor with 3.0 L of MTBE (1.0-1.5 Vol wrt Int-3). Charged Charcoal (0.45 kg; 15 w/w wrt Int-03). Stirred for NLT 20 min at 40° C. Filtered the solution through celite bed, rinse the container with 3 L (1.0-1.5 Vol wrt Int-3) of MTBE, filtered the rinse. Washed filter bed with MTBE (9 L; 3.0-3.5 Vol wrt Int-03). Concentrated the filtrate to around 2-3 volume stage (wrt Int-03) under vacuum at 35-40° C. Charged Acetonitrile (18 L, 6.0-6.5 Vol wrt Int-03). Continued concentration at 30-35° C. to around 2-3 vol stage[3] (wrt Int-03). Cooled the solution to 0° C. to 5° C. Maintained for NLT 15 min. Filtered the Solid, Washed solid with chilled Acetonitrile (0° C.) (9 L; 3 Vol wrt Int-03). Suck dried for 2 h, dried the product at 55° C. in VTD for 15 h. Wt: 3395 g (Yield-80.8%). Description (color and appearance): Off White solid. HPLC RT Time 6.362 min under following conditions: Detector: 210 nm; Injection volume 5.00 µL; Run Time 15 min; Column. YMC UltraHT Pro C18 (50 mm×3.0 mm), 2.0µ; Mobile Phase A—0.05% TFA in MillQ Water; Mobile Phase B—0.05% TFA in Acetonitrile; Flow: 1.0 mL/min; Column Oven—40° C.; Time (min)—0 05 10 12 15; B Conc.—10 90 90 10 10. NMR: ($^1$H NMR, 400 MHz, dmso-d$_6$) δ 8.122 (m, 2H), 7.62 (m, 2H), 7.42 (m, 2H); ($^{13}$C NMR, 100.64 MHz, dmso-d$_6$) δ 164.48, 162.00, 154.09, 154.02, 151.88, 149.36, 130.52, 130.44, 126.81, 125.67, 121.61, 121.45, 116.49, 116.28, 114.42, 114.27, 109.36, 109.32.

Example 2
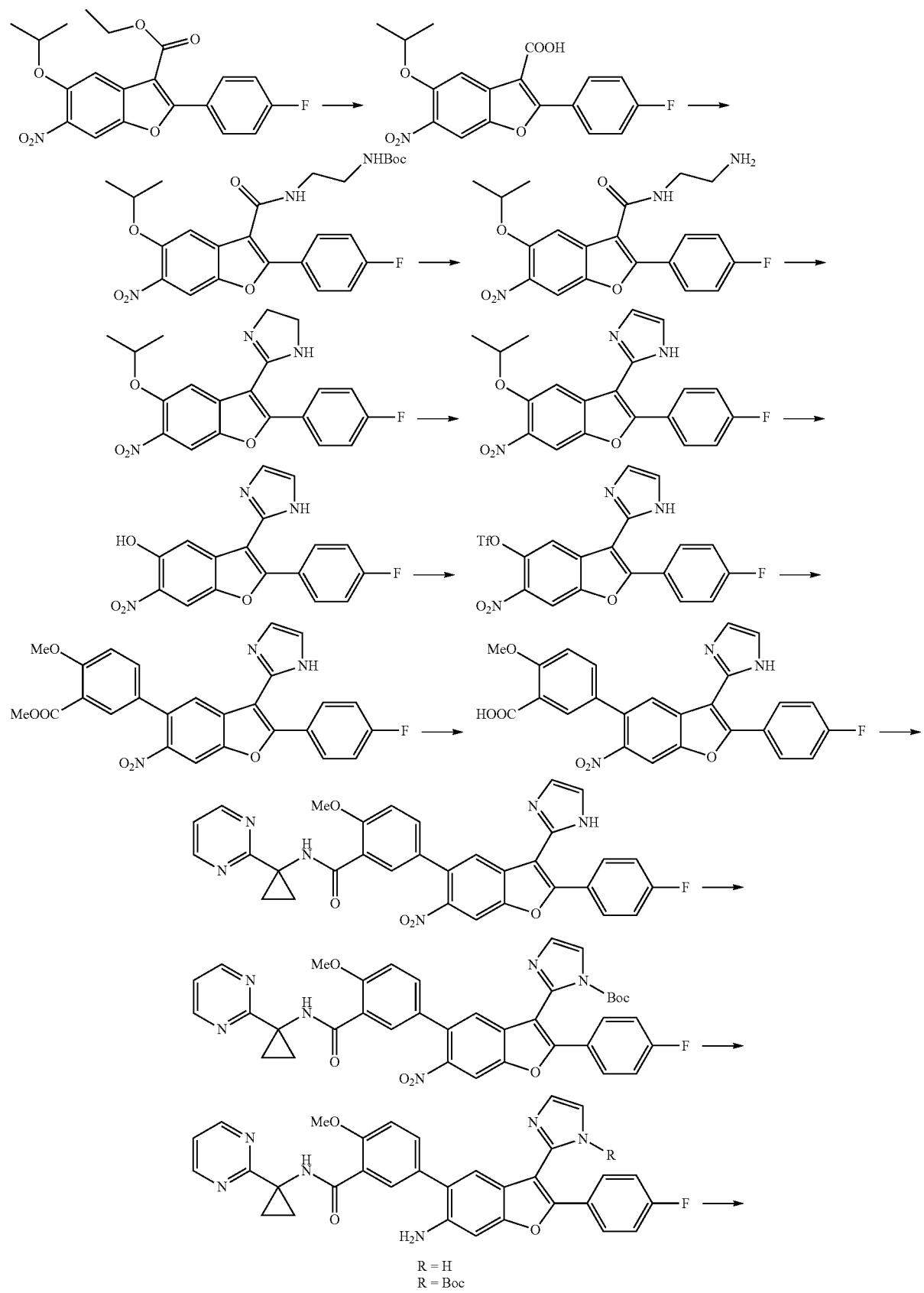
R = H
R = Boc

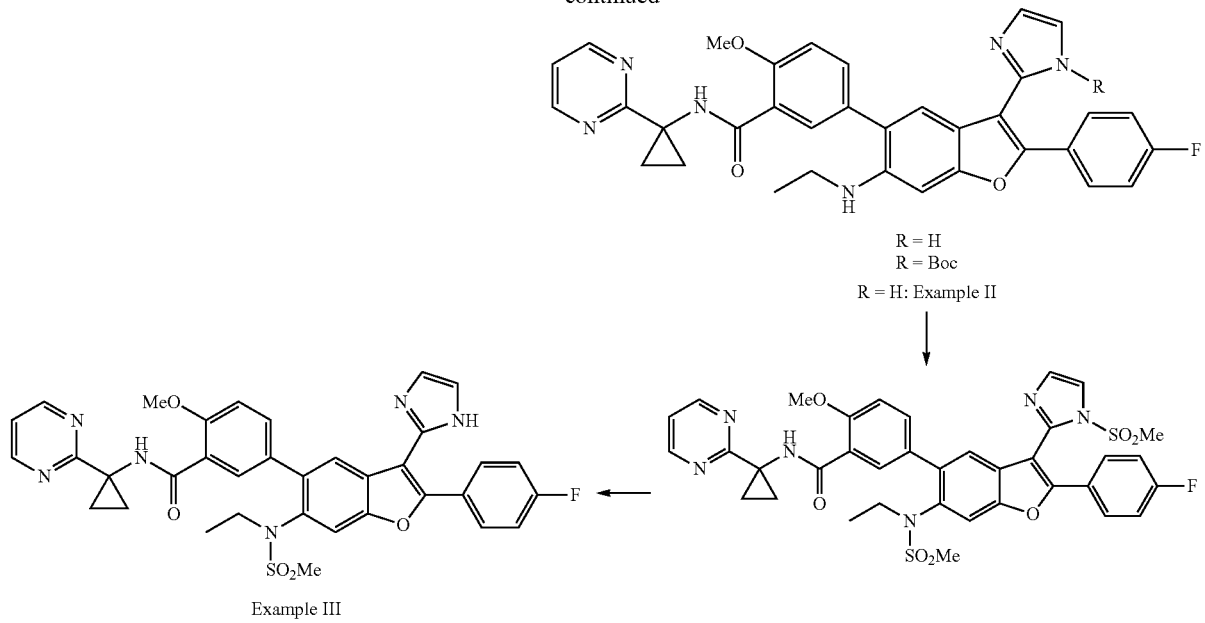

Example III

Preparation of 2-(4-fluorophenyl)-5-isopropoxy-6-nitrobenzofuran-3-carboxylic acid. An aqueous solution of sodium hydroxide (7.74 mL, 15.48 mmol, 2.0 M) was added to a mixture of ethyl 2-(4-fluorophenyl)-5-isopropoxy-6-nitrobenzofuran-3-carboxylate (1.5 g, 3.87 mmol) in a THF (50 mL)/Water (10 mL) mixture at room temperature. The reaction mixture was heated to 50° C. and maintained at the same temperature overnight. The reaction mixture was then concentrated to remove the solvent. The residue was diluted with water, acidified with 1.5 N HCl, stirred for 5 min and filtered. The solid was dried under suction to obtained title compound as a white solid. Yield: 1.35 g, (97%). $^1$H NMR (400 MHz, DMSO-$d_6$) δ ppm: 8.35 (s, 1H) 8.02-8.16 (m, 2H) 7.78 (s, 1H) 7.33-7.49 (m, 2H) 4.69-4.85 (m, 1H) 1.27-1.40 (m, 6H).

LCMS: (ES+) m/z=360.23 (M+H)$^+$; Column—ACQUITY UPLC BEH C8 (50×2.1 mm; 1.7 nm); Moblie (M) phase A: 5 mM Ammonium Acetate:MeCN (95:5); Moblie (M) phase B: 5 mM Ammonium Acetate:MeCN (5:95)
Flow: 0.8 ml/Min

| Time | % A | % B |
|------|-----|-----|
| 0.0  | 95  | 5   |
| 1.1  | 5   | 95  |
| 1.7  | 5   | 95  |

Retention Time (RT): 0.73 min, wavelength: 220 nm

Preparation of tert-butyl (2-(2-(4-fluorophenyl)-5-isopropoxy-6-nitrobenzofuran-3-carboxamido)ethyl)carbamate. To a mixture of 2-(4-fluorophenyl)-5-isopropoxy-6-nitrobenzofuran-3-carboxylic acid (1.3 g, 3.62 mmol), tert-butyl (2-aminoethyl)carbamate (0.696 g, 4.34 mmol) in DMF (50 mL) at room temperature was added N,N-diisopropylethylamine (DIPEA) (2.53 mL, 14.47 mmol). The mixture was cooled to 0° C., added with (benzotriazol-1-yloxy)tris(dimethylamino)phosphonium hexafluorophosphate (BOP) (2.40 g, 5.43 mmol), and then stirred at room temperature (rt) overnight. The reaction mixture was diluted with water, stirred for 5 min. The solid was filtered and dried under suction to obtain the title compound as a yellow solid. Yield: 1.6 g, (88%). $^1$H NMR (400 MHz, DMSO-$d_6$) δ ppm: 8.61 (t, J=5.65 Hz, 1H) 8.32 (s, 1H) 7.90-8.09 (m, 2H) 7.50 (s, 1H) 7.28-7.46 (m, 2H) 6.91 (t, J=5.65 Hz, 1H) 4.87 (dt, J=12.17, 5.96 Hz, 1H) 3.35-3.49 (m, 2H) 3.06-3.23 (m, 2H) 1.09-1.47 (m, 15H). LCMS: (ES+) m/z=502.34 (M+H)$^+$; Column—ACQUITY UPLC BEH C8 (50×2.1 mm; 1.7 nm); M phase A: 5 mM Ammonium Acetate: MeCN (95:5); M phase B: 5 mM Ammonium Acetate:MeCN (5:95)

| Time | % A | % B |
|------|-----|-----|
| 0.0  | 95  | 5   |
| 1.1  | 5   | 95  |
| 1.7  | 5   | 95  |

Preparation of N-(2-aminoethyl)-2-(4-fluorophenyl)-5-isopropoxy-6-nitrobenzofuran-3-carboxamide. To a mixture of tert-butyl (2-(2-(4-fluorophenyl)-5-isopropoxy-6-nitrobenzofuran-3-carboxamido)ethyl) carbamate (1.6 g, 3.19 mmol) in dioxane (50 mL) at room temperature was added 4.0 M HCl in dioxane (7.98 mL, 31.9 mmol). The reaction mixture was then stirred at rt overnight. The reaction mixture was diluted with water, and basified by using solid NaHCO$_3$. The product was extracted with EtOAc (100 mL×2), the organic extract washed with brine, dried over Na$_2$SO$_4$ and concentrated to obtain the title compound as a yellow solid. Yield: 1.2 g (94%). $^1$H NMR (400 MHz, DMSO-$d_6$) δ ppm: 8.52-8.69 (m, 1H) 8.31 (s, 1H) 7.95-8.08 (m, 2H) 7.54 (s, 1H) 7.40-7.46 (m, 2H) 4.79-4.90 (m, 1H) 3.34-3.45 (m, 3H) 3.16-3.24 (m, 1H) 2.78-2.86 (m, 2H) 1.31-1.38 (m, 6H).

LCMS: (ES+) m/z=402.28 (M+H)$^+$; Column—ACQUITY UPLC BEH C8 (50×2.1 mm; 1.7 nm); M phase A: 5 mM Ammonium Acetate:MeCN (95:5) M phase B: 5 mM Ammonium Acetate:MeCN (5:95)

Flow: 0.8 ml/Min

| Time | % A | % B |
| --- | --- | --- |
| 0.0 | 95 | 5 |
| 1.1 | 5 | 95 |
| 1.7 | 5 | 95 |

RT: 0.88 min, wavelength: 220 nm

Preparation of 2-(2-(4-fluorophenyl)-5-isopropoxy-6-nitrobenzofuran-3-yl)-4,5-dihydro-1H-imidazole. To a solution of N-(2-aminoethyl)-2-(4-fluorophenyl)-5-isopropoxy-6-nitrobenzofuran-3-carboxamide (1.2 g, 2.99 mmol) in toluene (75 mL) at room temperature under nitrogen was added POCl$_3$ (2.79 mL, 29.9 mmol). The reaction mixture was heated to 100° C. and maintained at same temperature overnight. The reaction mixture was concentrated completely under vacuum, and the residue diluted with water, basified with NaHCO$_3$. The product was extracted with EtOAc (100 mL×3), washed with brine, dried over Na$_2$SO$_4$ and concentrated to obtain 2-(2-(4-fluorophenyl)-5-isopropoxy-6-nitrobenzofuran-3-yl)-4,5-dihydro-1H-imidazole as a yellow solid. Yield: 1.0 g (87%). LCMS: (ES+) m/z=384.28 (M+H)$^+$; Column—ACQUITY UPLC BEH C8 (50×2.1 mm; 1.7 nm); M phase A: 5 mM Ammonium Acetate:MeCN (95:5); M phase B: 5 mM Ammonium Acetate:MeCN (5:95)
Flow: 0.8 ml/Min

| Time | % A | % B |
| --- | --- | --- |
| 0.0 | 95 | 5 |
| 1.1 | 5 | 95 |
| 1.7 | 5 | 95 |

RT: 0.93 min, wavelength: 220 nm

Preparation of 2-(2-(4-fluorophenyl)-5-isopropoxy-6-nitrobenzofuran-3-yl)-1H-imidazole. To a stirred solution of 2-(2-(4-fluorophenyl)-5-isopropoxy-6-nitrobenzofuran-3-yl)-4,5-dihydro-1H-imidazole (1.0 g, 2.61 mmol) in DMSO (40 mL) at room temperature was added Dess-Martin periodinane (2.213 g, 5.22 mmol), and the stirring was continued at rt overnight. The reaction mixture was diluted with water. The product was extracted into EtOAc (100 mL×3), and the combined EtOAc extracts were washed with 10% NaHCO$_3$ (100 mL×2) and brine, dried over Na$_2$SO$_4$ and then concentrated. The crude product was recrystallized from EtOAc and petroleum ethers to obtain 2-(2-(4-fluorophenyl)-5-isopropoxy-6-nitrobenzofuran-3-yl)-1H-imidazole as a yellow solid. Yield: 800 mg (80%). $^1$H NMR (300 MHz, DMSO-d$_6$) δ ppm: 12.46 (br. s., 1H) 8.33 (s, 1H) 7.85-8.08 (m, 2H) 7.16-7.60 (m, 5H) 4.79 (d, J=5.95 Hz, 1H) 1.15-1.47 (m, 6H). LCMS: (ES+) m/z=382.24 (M+H)$^+$; Column—ACQUITY UPLC BEH C8 (50×2.1 mm; 1.7 µm); M phase A: 5 mM Ammonium Acetate:MeCN (95:5); M phase B: 5 mM Ammonium Acetate:MeCN (5:95)
Flow: 0.8 ml/Min

| Time | % A | % B |
| --- | --- | --- |
| 0.0 | 95 | 5 |
| 1.1 | 5 | 95 |
| 1.7 | 5 | 95 |

RT: 1.08 min, wavelength: 220 nm

Preparation of 2-(4-fluorophenyl)-3-(1H-imidazol-2-yl)-6-nitrobenzofuran-5-ol. To a solution of 2-(2-(4-fluorophenyl)-5-isopropoxy-6-nitrobenzofuran-3-yl)-1H-imidazole (800 mg, 2.098 mmol) in dichloromethane (DCM) (80 mL) at −78° C. under an nitrogen atmosphere was added a 1.0 M solution of trichloroborane in DCM (5.24 mL, 5.24 mmol). The reaction mixture was allowed to warm to room temperature and stirring continued at rt overnight. The reaction mixture was then concentrated completely to remove the volatiles. The residue was diluted with ice-cold water, and the solid filtered to obtain the title compound as a yellow solid. Yield: 650 mg (91%). $^1$H NMR (400 MHz, DMSO-d$_6$) δ ppm: 14.59-15.34 (m, 1H) 11.07 (br s, 1H) 8.35-8.52 (m, 1H) 8.07 (d, J=1.76 Hz, 1H) 7.87-7.99 (m, 1H) 7.59-7.77 (m, 1H) 7.30-7.55 (m, 4H). LCMS: (ES+) m/z=340.15 (M+H)$^+$; Column—ACQUITY UPLC BEH C8 (50×2.1 mm; 1.7 µm); M phase A: 5 mM Ammonium Acetate:MeCN (95:5); M phase B: 5 mM Ammonium Acetate:MeCN (5:95)
Flow: 0.8 ml/Min

| Time | % A | % B |
| --- | --- | --- |
| 0.0 | 95 | 5 |
| 1.1 | 5 | 95 |
| 1.7 | 5 | 95 |

RT: 0.95 min, wavelength: 220 nm

Preparation of 2-(4-fluorophenyl)-6-nitro-3-(1-((trifluoromethyl)sulfonyl)-1H-imidazol-2-yl)benzofuran-5-yl trifluoromethanesulfonate. To a mixture of 2-(4-fluorophenyl)-3-(1H-imidazol-2-yl)-6-nitrobenzofuran-5-ol (650 mg, 1.916 mmol) in pyridine (60 mL) at room temperature was added N,N-dimethylaminopyridine (DMAP) (234 mg, 1.916 mmol). The mixture was then cooled to 0° C. and added with triflic anhydride (0.647 mL, 3.83 mmol). The reaction mixture was allowed to warm to room temperature and stirring continued at rt for 24 hr. The reaction mixture was diluted with water, and stirred for 10 min. The solid was filtered, washed with water and dried under suction. The crude product was purified by combiflash using a mixture of EtOAc/petroleum ether as an eluant over a 24 g silica column. The titled compound was collected at 14% EtOAc in pet. ether and concentrated. Yield: 500 mg (43%). $^1$H NMR (400 MHz, DMSO-d$_6$) δ ppm: 8.90 (s, 1H) 8.24-8.41 (m, 2H) 7.65-7.82 (m, 3H) 7.34-7.52 (m, 2H). LCMS: (ES+) m/z=604.06 (M+H)$^+$; Column—ACQUITY UPLC BEH C8 (50×2.1 mm; 1.7 µm); M phase A: 5 mM Ammonium Acetate:MeCN (95:5); M phase B: 5 mM Ammonium Acetate:MeCN (5:95)
Flow: 0.8 ml/Min

| Time | % A | % B |
| --- | --- | --- |
| 0.0 | 95 | 5 |
| 1.1 | 5 | 95 |
| 1.7 | 5 | 95 |

RT: 1.29 min, wavelength: 220 nm

Preparation of methyl 5-(2-(4-fluorophenyl)-3-(1H-imidazol-2-yl)-6-nitrobenzofuran-5-yl)-2-methoxybenzoate. A mixture of 2-(4-fluorophenyl)-6-nitro-3-(1-((trifluoromethyl)sulfonyl)-1H-imidazol-2-yl)benzofuran-5-yl trifluoromethanesulfonate (500 mg, 0.829 mmol), methyl 2-methoxy-5-(4,4,5,5-tetramethyl-1,3,2-dioxaborolan-2-yl) benzoate (290 mg, 0.994 mmol), potassium phosphate (352 mg, 1.657 mmol) in a mixture of dioxane (40 mL)/water (4 mL) in a pressure tube at rt was degassed, and then added with PdCl$_2$(dppf)-CH$_2$Cl$_2$ adduct (67.7 mg, 0.083 mmol). The reaction mixture was heated to 100° C. and maintained at the same temperature overnight. The reaction mixture was filtered through celite, and the celite bed washed with EtOAc. The filtrate was concentrated, and the residue was purified by Combiflash using a mixture of petroleum ether and EtOAc as an eluant and a 40 g silica column. The title compound was collected at 70% EtOAc in pet. ether. Yield: 375 mg (93%). $^1$H NMR (400 MHz, DMSO-$d_6$) δ ppm: 12.52 (br s, 1H) 8.52 (s, 1H) 8.10-8.20 (m, 1H) 7.58-7.82 (m, 2H) 7.56 (dd, J=8.53, 2.51 Hz, 1H) 7.36-7.47 (m, 4H) 7.18-7.32 (m, 2H) 3.89 (s, 3H) 3.80 (s, 3H); LCMS: (ES−) m/z=486.0 (M−H); Column—Acentis Express C8 (50×2.1 mm; 2.7 u); M phase A: 10 mM Ammonium Formate in Water:MeCN (90:10); M phase B: 10 mM Ammonium Formate in Water:MeCN (10:90)
Flow: 1 ml/Min

| Time | % A | % B |
|---|---|---|
| 0.0 | 100 | 0 |
| 1.6 | 0 | 100 |
| 3.2 | 0 | 100 |
| 3.6 | 100 | 0 |

RT: 1.95 min, wavelength: 220 nm

Preparation of 5-(2-(4-fluorophenyl)-3-(1H-imidazol-2-yl)-6-nitrobenzofuran-5-yl)-2-methoxybenzoic acid. To a mixture of methyl 5-(2-(4-fluorophenyl)-3-(1H-imidazol-2-yl)-6-nitrobenzofuran-5-yl)-2-methoxybenzoate (370 mg, 0.759 mmol) in a mixture of THF (40 mL)/water (4 mL) at room temperature was added a 2.0 M aqueous sodium hydroxide solution (1.518 mL, 3.04 mmol). The reaction mixture was heated to 50° C. and maintained at the same temperature overnight. The reaction mixture was concentrated to remove the solvent. The residue was diluted with water, acidified by using 1.5 N HCl, filtered and dried under suction to give the title compound as a yellow solid. Yield: 320 mg (89%). $^1$H NMR (400 MHz, DMSO-$d_6$) δ ppm: 13.11-13.73 (m, 1H) 12.66-12.97 (m, 1H) 8.53 (s, 1H) 7.94-8.09 (m, 2H) 7.63-7.82 (m, 1H) 7.34-7.51 (m, 5H) 7.23 (d, J=8.78 Hz, 2H) 3.88 (s, 3H). LCMS: (ES+) m/z=474.23 (M+H)$^+$; Column—ACQUITY UPLC BEH C8 (50×2.1 mm; 1.7 nm); Mphase A: 5 mM Ammonium Acetate:MeCN (95:5); Mphase B: 5 mM Ammonium Acetate:MeCN (5:95)
Flow: 0.8 ml/Min

| Time | % A | % B |
|---|---|---|
| 0.0 | 95 | 5 |
| 1.1 | 5 | 95 |
| 1.7 | 5 | 95 |

RT: 0.72 min, wavelength: 220 nm

Preparation of 5-(2-(4-fluorophenyl)-3-(1H-imidazol-2-yl)-6-nitrobenzofuran-5-yl)-2-methoxy-N-(1-(pyrimidin-2-yl)cyclopropyl)benzamide. To a mixture of 5-(2-(4-fluorophenyl)-3-(1H-imidazol-2-yl)-6-nitrobenzofuran-5-yl)-2-methoxybenzoic acid (300 mg, 0.634 mmol) and 1-(pyrimidin-2-yl)cyclopropanamine hydrochloride (131 mg, 0.760 mmol) in DMF (15 mL) at room temperature under a nitrogen atmosphere was added triethylamine (TEA) (0.442 mL, 3.17 mmol). The mixture was cooled to 0° C. and added with BOP reagent (420 mg, 0.951 mmol). The reaction mixture was then stirred at rt overnight, and then diluted with water. The solid was filtered and dried under suction to obtain the title compound as a light yellow solid. Yield: 350 mg (94%). $^1$H NMR (400 MHz, DMSO-$d_6$) δ ppm: 12.52 (br. s, 1H) 8.93 (s, 1H) 8.70 (s, 2 H) 8.49 (s, 1H) 8.00-8.14 (m, 2H) 7.88 (d, J=2.51 Hz, 1H) 7.74 (s, 1H) 7.52 (dd, J=8.53, 2.51 Hz, 1H) 7.34-7.43 (m, 4H) 7.20 (s, 1H) 3.89 (s, 3H) 1.54-1.68 (m, 2H) 1.36-1.49 (m, 2H). LCMS: (ES+) m/z=591.39 (M+H)$^+$; Column—ACQUITY UPLC BEH C8 (50×2.1 mm; 1.7 μm); Mphase A: 5 mM Ammonium Acetate:MeCN (95:5); Mphase B: 5 mM Ammonium Acetate: MeCN (5:95)
Flow: 0.8 ml/Min

| Time | % A | % B |
|---|---|---|
| 0.0 | 95 | 5 |
| 1.1 | 5 | 95 |
| 1.7 | 5 | 95 |

RT: 1.0 min, wavelength: 220 nm

Preparation of tert-butyl 2-(2-(4-fluorophenyl)-5-(4-methoxy-3-((1-(pyrimidin-2-yl)cyclopropyl)carbamoyl)phenyl)-6-nitrobenzofuran-3-yl)-1H-imidazole-1-carboxylate. To a solution of 5-(2-(4-fluorophenyl)-3-(1H-imidazol-2-yl)-6-nitrobenzofuran-5-yl)-2-methoxy-N-(1-(pyrimidin-2-yl)cyclopropyl)benzamide (350 mg, 0.593 mmol) in THF (35 mL) at room temperature was added DMAP (72.4 mg, 0.593 mmol) followed by di-tert-butyl dicarbonate (194 mg, 0.889 mmol), and the resulting mixture stirred at rt overnight. The reaction mixture was concentrated, and the crude product was purified via combiflash using a mixture of CHCl$_3$/MeOH as an eluant and a 24 g silica column. The title compound was collected at 2.0% MeOH in CHCl$_3$ as an off white solid. Yield: 330 mg (81%). $^1$H NMR (400 MHz, DMSO-$d_6$) δ ppm: 8.92 (s, 1H) 8.69 (d, J=4.77 Hz, 2H) 8.55 (s, 1H) 7.86 (d, J=1.51 Hz, 1H) 7.81 (d, J=2.51 Hz, 1H) 7.58-7.70 (m, 2H) 7.56 (s, 1H) 7.31-7.47 (m, 3H) 7.15-7.28 (m, 3H) 4.01 (s, 3H) 1.56-1.67 (m, 2H) 1.41-1.48 (m, 2H) 1.10 (s, 9H); LCMS: (ES+) m/z observed=591.35 (M+H)$^+$ of 5-(2-(4-fluorophenyl)-3-(1H-imidazol-2-yl)-6-nitrobenzofuran-5-yl)-2-methoxy-N-(1-(pyrimidin-2-yl)cyclopropyl)benzamide; Column—ACQUITY UPLC BEH C8 (50×2.1 mm; 1.7 μm); M phase A: 5 mM Ammonium Acetate:MeCN (95:5); M phase B: 5 mM Ammonium Acetate:MeCN (5:95)
Flow: 0.8 ml/Min

| Time | % A | % B |
|---|---|---|
| 0.0 | 95 | 5 |
| 1.1 | 5 | 95 |
| 1.7 | 5 | 95 |

RT: 1.18 min, wavelength: 220 nm

Preparation of tert-butyl 2-(6-amino-2-(4-fluorophenyl)-5-(4-methoxy-3-((1-(pyrimidin-2-yl)cyclopropyl)carbamoyl)phenyl)benzofuran-3-yl)-1H-imidazole-1-carboxylate and 5-(6-amino-2-(4-fluorophenyl)-3-(1H-imidazol-2-yl)benzofuran-5-yl)-2-methoxy-N-(1-(pyrimidin-2-yl)cyclopropyl)benzamide. A mixture of tert-butyl 2-(2-(4-fluorophenyl)-5-(4-methoxy-3-((1-(pyrimidin-2-yl)cyclopropyl)carbamoyl)phenyl)-6-nitrobenzofuran-3-yl)-1H-imidazole-1-carboxylate (300 mg, 0.434 mmol), EtOH (30 mL) and ammonium chloride (232 mg, 4.34 mmol) at room temperature in a sealed tube was stirred for 5 min and then added with indium powder (249 mg, 2.172 mmol) at rt. The reaction mixture was heated to 90° C. and stirred at the same temperature overnight. The reaction mixture was concentrated to remove EtOH. The residue was diluted with water, filtered and the solid dried under suction to obtain a mixture of ten-butyl 2-(6-amino-2-(4-fluorophenyl)-5-(4-methoxy-3-((1-(pyrimidin-2-yl)cyclopropyl)carbamoyl)phenyl)benzofuran-3-yl)-1H-imidazole-1-carboxylate and 5-(6-amino-2-(4-fluorophenyl)-3-(1H-imidazol-2-yl)benzofuran-5-yl)-2-methoxy-N-(1-(pyrimidin-2-yl)cyclopropyl)benzamide as a yellow solid (260 mg). LCMS: (ES−) m/z=559.2 (M−H); Column—Acentis Express C8 (50×2.1 mm; 2.7 u); M phase A: 2% MeCN-98% H$_2$O-10 mM NH$_4$COOH; M phase B: 98% MeCN-2% H$_2$O-10 mM NH$_4$COOH
Flow: 1 ml/Min

| Time | % A | % B |
|---|---|---|
| 0.0 | 100 | 0 |
| 1.5 | 0 | 100 |
| 3.2 | 0 | 100 |

RT: 1.95 and 2.09 min, wavelength: 220 nm

Preparation of 5-(6-(ethylamino)-2-(4-fluorophenyl)-3-(1H-imidazol-2-yl)benzofuran-5-yl)-2-methoxy-N-(1-(pyrimidin-2-yl)cyclopropyl)benzamide. The above obtained mixture of tert-butyl 2-(6-amino-2-(4-fluorophenyl)-5-(4-methoxy-3-((1-(pyrimidin-2-yl)cyclopropyl)carbamoyl)phenyl)benzofuran-3-yl)-1H-imidazole-1-carboxylate and 5-(6-amino-2-(4-fluorophenyl)-3-(1H-imidazol-2-yl)benzofuran-5-yl)-2-methoxy-N-(1-(pyrimidin-2-yl)cyclopropyl)benzamide (170 mg, 0.257 mmol) in MeOH (25 mL) was cooled to 0° C. and then added with acetaldehyde (45.3 mg, 1.029 mmol). The reaction mixture was allowed to warm to rt and stirred for 45 min. The reaction mixture was again cooled to 0° C. and then added with sodium cyanoborohydride (32.3 mg, 0.515 mmol). The reaction mixture was allowed to warm to rt and stirring continued at rt for 2 hr. The reaction mixture was concentrated completely at reduced pressure at 35° C. The residue was diluted with water and 10% NaHCO$_3$ solution, filtered, and the solid obtained dried under suction. The crude product was purified by preparative HPLC to separate the two compounds. $^1$H NMR (400 MHz, DMSO-d$_6$) δ ppm: 12.32 (br s, 1H) 8.92 (s, 1H) 8.69 (d, J=4.8 Hz, 2H) 7.94-8.03 (m, 2H) 7.86 (d, J=2.51 Hz, 1H) 7.55 (dd, J=8.53, 2.51 Hz, 1H) 7.22-7.33 (m, 5H) 7.21 (s, 1H) 7.13 (s, 1H) 6.91 (s, 1H) 4.58 (t, J=5.65 Hz, 1H) 3.99 (s, 3H) 3.13-3.22 (m, 2H) 1.59-1.66 (m, 2H) 1.38-1.46 (m, 2H) 1.10-1.21 (m, 3H). $^{19}$F NMR (376.6 MHz, DMSO-d$_6$) δ ppm: 112.76. LCMS: (ES−) m/z=587.2 (M−H); Column—Acentis Express C8 (50×2.1 mm; 2.7 u); M phase A: 2% MeCN-98% H$_2$O-10 mM NH$_4$COOH; M phase B: 98% MeCN-2% H$_2$O-10 mM NH$_4$COOH
Flow: 1 ml/Min

| Time | % A | % B |
|---|---|---|
| 0.0 | 100 | 0 |
| 1.5 | 0 | 100 |
| 3.2 | 0 | 100 |

RT: 1.94 min, wavelength: 220 nm tert-Butyl 2-(6-(ethylamino)-2-(4-fluorophenyl)-5-(4-methoxy-3-((1-(pyrimidin-2-yl)cyclopropyl)carbamoyl)phenyl)benzofuran-3-yl)-1H-imidazole-1-carboxylate (Yield: 30 mg). $^1$H NMR (400 MHz, DMSO-d$_6$) δ ppm: 8.91 (s, 1H) 8.68 (d, J=5.02 Hz, 2H) 7.70-7.90 (m, 2H) 7.39-7.65 (m, 3H) 7.19-7.39 (m, 5H) 6.70-7.08 (m, 2H) 4.55 (t, J=5.52 Hz, 1H) 3.97 (s, 3H) 3.18 (quin, J=6.65 Hz, 2H) 1.61 (q, J=3.68 Hz, 2H) 1.41 (q, J=3.93 Hz, 2H) 1.18-1.33 (m, 3H) 0.92-1.16 (m, 9H). LCMS: (ES+) m/z observed=589.2 (M+H)$^+$ of 5-(6-(ethylamino)-2-(4-fluorophenyl)-3-(1H-imidazol-2-yl)benzofuran-5-yl)-2-methoxy-N-(1-(pyrimidin-2-yl)cyclopropyl)benzamide; Column—Acentis Express C8 (50×2.1 mm; 2.7 u); Mphase A: 2% MeCN-98% H$_2$O-10 mM NH$_4$COOH; Mphase B: 98% MeCN-2% H$_2$O-10 mM NH$_4$COOH
Flow: 1 ml/Min

| Time | % A | % B |
|---|---|---|
| 0.0 | 100 | 0 |
| 1.5 | 0 | 100 |
| 3.2 | 0 | 100 |

RT: 2.18 min, wavelength: 220 nm

Example 3

Preparation of 5-(6-(N-ethylmethylsulfonamido)-2-(4-fluorophenyl)-3-(1-(methylsulfonyl)-1H-imidazol-2-yl)benzofuran-5-yl)-2-methoxy-N-(1-(pyrimidin-2-yl)cyclopropyl)benzamide. To a solution of 5-(6-(ethylamino)-2-(4-fluorophenyl)-3-(1H-imidazol-2-yl)benzofuran-5-yl)-2-methoxy-N-(1-(pyrimidin-2-yl)cyclopropyl)benzamide (40 mg, 0.068 mmol) in pyridine (3.0 mL) at room temperature was added DMAP (16.60 mg, 0.136 mmol) followed by methanesulfonyl chloride (7.94 μl, 0.102 mmol). The reaction mixture was stirred at rt overnight, and then diluted with water. The mixture was extracted with EtOAc, and the organic extract washed with brine, dried over Na$_2$SO$_4$ and concentrated to obtain the title compound as an off white solid. Yield: 45 mg (89%). LCMS: (ES+) m/z=745.2 (M+H)$^+$; Column—ACE Excel 2 C18 (50×3.0 mm-2 μm); M phase A: 2% MeCN-98% H$_2$O-10 mM NH$_4$COOH; M phase B: 98% MeCN-2% H$_2$O-10 mM NH$_4$COOH
Flow: 1 ml/Min

| Time | % A | % B |
|---|---|---|
| 0.0 | 100 | 0 |
| 1.8 | 0 | 100 |
| 2.6 | 0 | 100 |
| 3.6 | 95 | 5 |
| 4.0 | 95 | 5 |

RT: 2.09 min, wavelength: 220 nm

Preparation of 5-(6-(N-ethylmethylsulfonamido)-2-(4-fluorophenyl)-3-(1H-imidazol-2-yl)benzofuran-5-yl)-2-methoxy-N-(1-(pyrimidin-2-yl)cyclopropyl)benzamide. To a solution of 5-(6-(N-ethylmethylsulfonamido)-2-(4-fluorophenyl)-3-(1-(methylsulfonyl)-1H-imidazol-2-yl)benzofuran-5-yl)-2-methoxy-N-(1-(pyrimidin-2-yl)cyclopropyl) benzamide (40 mg, 0.054 mmol) in THF (2.5 mL) at 0° C. was added TBAF (0.269 mL, 0.269 mmol, 1.0 M in THF), and the reaction mixture maintained at the same temperature for 30 min. The reaction mixture was diluted with water and extracted with EtOAc. The organic extract was washed with brine, dried over Na$_2$SO$_4$ and concentrated. The crude product was purified by Prep HPLC. Yield: 4.5 mg (13%).

$^1$H NMR (400 MHz, DMSO-d$_6$) δ ppm: 12.45 (br s, 1H) 8.88 (s, 1H) 8.68 (d, J=4.77 Hz, 2H) 8.05 (dd, J=8.78, 5.52 Hz, 2H) 7.95 (d, J=2.4 Hz, 1H) 7.93 (s, 1H) 7.68 (dd, J=8.66, 2.13 Hz, 1H) 7.59 (s, 1H) 7.38 (t, J=8.8 Hz, 2H) 7.33 (s, 1H) 7.24-7.30 (m, 2H) 7.18 (s, 1H) 4.00 (s, 3H) 3.52 (br s, 2H) 3.10 (s, 3H) 1.60 (appeared as d, J=3.01 Hz, 2H) 1.43 (appeared as d, J=3.01 Hz, 2H) 0.93 (t, J=7.15 Hz, 3H). $^{19}$F NMR (376.6 MHz, DMSO-d$_6$) δ ppm: 100.72. HPLC Method: XBridege phenyl (4.6×150) mm, 3.5 micron; Buffer: 0.05%

TFA in water pH 2.5; Mobile Phase A: Buffer: MeCN (95:5); Mobile Phase B: MeCN: Buffer (95:5)
Flow: 1 ml/min

| Time | B % |
|---|---|
| 0 | 10 |
| 12 | 100 |
| 15 | 100 |

Wavelength: 254 nm, RT: 7.92 min; Wavelength: 220 nm, RT: 7.92 min

HPLC Method: SUNFIRE C18 (4.6×150) mm, 3.5 micron; Buffer: 0.05% TFA in water pH 2.5; Mobile Phase A: Buffer: MeCN (95:5); Mobile Phase B: MeCN: Buffer (95:5); Flow: 1 ml/min

| Time | B % |
|---|---|
| 0 | 10 |
| 12 | 100 |
| 15 | 100 |

Wavelength: 254 nm, RT: 6.73 min; Wavelength: 220 nm, RT: 6.73 min

Biological Methods

HCV NS5B RdRp Cloning, Expression, and Purification

The cDNA encoding the NS5B protein of HCV, genotype 1b, was cloned into the pET21a expression vector. The protein was expressed with an 18 amino acid C-terminal truncation to enhance the solubility. The *E. coli* competent cell line BL21(DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 µg/mL and the cells were grown overnight at 20° C.

Cell pellets (3 L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/mL lysozyme, 10 mM $MgCl_2$, 15 ug/mL deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 30 minutes at 4° C. and filtered through a 0.2 µm filter unit (Corning).

The protein was purified using two sequential chromatography steps: Heparin sepharose CL-6B and polyU sepharose 4B. The chromatography buffers were identical to the lysis buffer but contained no lysozyme, deoxyribonuclease I, $MgCl_2$ or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

HCV NS5B RdRp Enzyme Assay.

An on-bead solid phase homogeneous assay was used in a 384-well format to assess NS5B inhibitors (Wang Y-K, Rigat K, Roberts S, and Gao M (2006) Anal Biochem, 359: 106-111). The biotinylated oligo $dT_{12}$ primer was captured on streptavidin-coupled imaging beads (GE, RPNQ0261) by mixing primer and beads in 1× buffer and incubating at room temperature for three hours. Unbound primer was removed after centrifugation. The primer-bound beads were resuspended in 3× reaction mix (20 mM Hepes buffer, pH 7.5, dT primer coupled beads, poly A template, $^3$H-UTP, and RNAse inhibitor (Promega N2515)). Compounds were serially diluted 1:3 in DMSO and aliquoted into assay plates. Equal volumes (10 µL) of water, 3× reaction mix, and enzyme in 3× assay buffer (60 mM Hepes buffer, pH 7.5, 7.5 mM $MgCl_2$, 7.5 mM KCl, 3 mM DTT, 0.03 mg/mL BSA, 6% glycerol) were added to the diluted compound on the assay plate. Final concentration of components in 384-well assay: 0.36 nM template, 15 nM primer, 0.29 µM $^3$H-UTP (0.3 µCi), 1.6 U/µL RNAse inhibitor, 7 nM NS5B enzyme, 0.01 mg/mL BSA, 1 mM DTT, and 0.33 µg/µL beads, 20 mM Hepes buffer, pH 7.5, 2.5 mM $MgCl_2$, 2.5 mM KCl, and 0.1% DMSO.

Reactions were allowed to proceed for 4 hours at 30° C. and terminated by the addition of 50 mM EDTA (10 µL). After incubating for at least 15 minutes, plates were read on an Amersham LEADseeker multimodality imaging system.

$IC_{50}$ values for compounds were determined using ten different [I]. $IC_{50}$ values were calculated from the inhibition using the four-parameter logistic formula $y=A+((B-A)/(1+((C/x)^D)))$, where A and B denote minimal and maximal % inhibition, respectively, C is the $IC_{50}$, D is hill slope and x represents compound concentration.

Cell Lines.

The cell lines used to evaluate compounds consist of a human hepatocyte derived cell line (Huh-7) that constitutively expresses a genotype 1b HCV replicon containing a *Renilla luciferase* reporter gene. These cells were maintained in Dulbecco's modified Eagle medium (DMEM) containing 10% FBS, 100 U/mL penicillin/streptomycin and 1.0 mg/mL G418.

HCV Replicon Luciferase Assay.

To evaluate compound efficacy, titrated compounds were transferred to sterile 384-well tissue culture treated plates, and the plates were seeded with HCV replicon cells (50 µL at a density of 2.4×$10^3$ cells/well) in DMEM containing 4% FBS (final DMSO concentration at 0.5%). After 3 days incubation at 37° C., cells were analyzed for *Renilla Luciferase* activity using the EnduRen substrate (Promega cat #E6485) according to the manufacturer's directions. Briefly, the EnduRen substrate was diluted in DMEM and then added to the plates to a final concentration of 7.5 µM. The plates were incubated for at least 1 h at 37° C. then read on a Viewlux Imager (PerkinElmer) using a luminescence program. The 50% effective concentration ($EC_{50}$) was calculated using the four-parameter logistic formula noted above.

To assess cytotoxicity of compounds, Cell Titer-Blue (Promega) was added to the EnduRen-containing plates and incubated for at least 4 hrs at 37° C. The fluorescence signal from each well was read using a Viewlux Imager. All $CC_{50}$ values were calculated using the four-parameter logistic formula.

Enzyme and replicon data for compounds I, II, and III is reported in Table 2.

TABLE 2

| Structure | EC$_{50}$, (μM) | IC$_{50}$ (μM) |
|---|---|---|
| 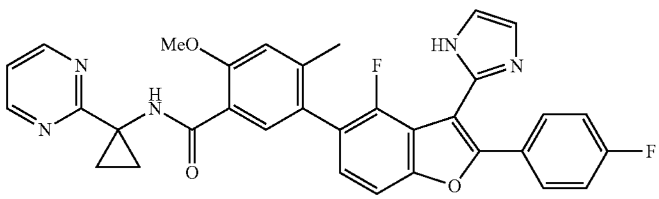 [SMILES: COc1cc(C)c(-c2ccc3oc(-c4ccc(F)cc4)c(-c4ncc[nH]4)c3c2F)cc1C(=O)NC1(c2ncccn2)CC1] | 0.030 | 0.030 |
| 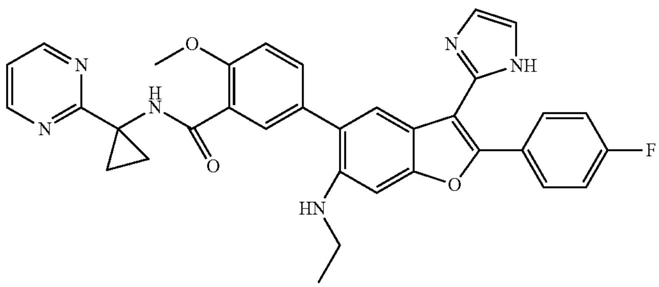 [SMILES: CCNc1cc2oc(-c3ccc(F)cc3)c(-c3ncc[nH]3)c2cc1-c1ccc(OC)c(C(=O)NC2(c3ncccn3)CC2)c1] | 0.0072 | NT |
| 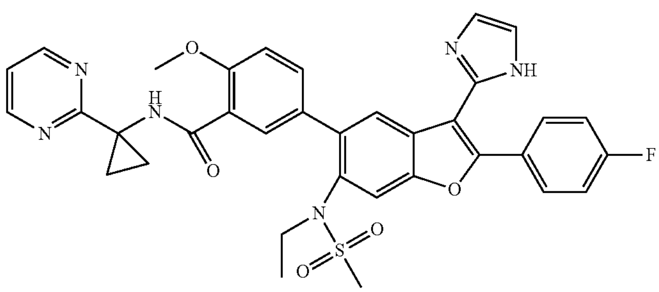 [SMILES: CCN(c1cc2oc(-c3ccc(F)cc3)c(-c3ncc[nH]3)c2cc1-c1ccc(OC)c(C(=O)NC2(c3ncccn3)CC2)c1)S(C)(=O)=O] | 0.0090 | NT |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula I

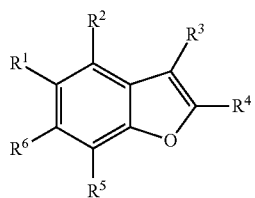

I where:
R1 is phenyl substituted with 0-3 substituents selected from the group consisting of halo, alkyl and alkoxy, and is also and is also substituted with 1 CON(R$^9$)(R$^{10}$) substituent;
R$^2$ is hydrogen, halo, alkyl, or alkoxy;
R$^3$ is imidazol-2-yl substituted with 0-3 halo or alkyl substituents;
R$^4$ is phenyl that is para substituted with halo;
R$^5$ is hydrogen;
R$^6$ is hydrogen, nitro, halo, alkyl, alkoxy, N(R$^7$)(R$^8$), or alkylsulfonyl;
R$^7$ and R$^8$ are independently hydrogen, alkyl, cyanoalkyl, haloalkyl, (cycloalkyl)alkyl, cycloalkyl, hydroxyalkyl, alkoxyalkyl, alkylcarbonyl, alkoxycarbonyl, haloalkoxycarbonyl, alkylsulfonyl, alkylsulfonylalkyl, SO$_2$N(R$^{13}$)(R$^{14}$), or benzyl where said benzyl is substituted with 0-3 substituents selected from halo, alkyl, haloalkyl, alkoxy, haloalkoxy, carboxy, and alkoxycarbonyl;
or N(R$^7$)(R$^8$) taken together is azetidinyl, pyrrolidinyl, piperidinyl, or piperazinyl, and is substituted with 0-2 substituents selected from alkyl, hydroxyalkyl, or hydroxy;
R$^9$ is

R$^{10}$ is hydrogen;
R$^{11}$ is hydrogen, alkyl, hydroxyalkyl, or alkoxyalkyl;
R$^{12}$ is hydrogen, alkyl, hydroxyalkyl, or alkoxyalkyl;
or R$^{11}$ and R$^{12}$ taken together is ethylene, propylene, butylenes, or pentylene substituted with 0-2 halo or alkoxy;

or $R^{11}$ and $R^{12}$ taken together is —$CH_2OCH_2$—, —$OCH_2CH_2$—, —$CH_2OCH_2CH_2$—, —$OCH_2CH_2CH_2$—, —$OCH_2CH_2CH_2CH_2$—, —$CH_2OCH_2CH_2CH_2$—, or —$CH_2CH_2OCH_2CH_2$—;

$R^{13}$ is hydrogen or alkyl;

$R^{14}$ is hydrogen or alkyl; and $Ar^2$ is phenyl, pyridinyl, or pyrimidinyl, and is substituted with 0-3 substituents selected from halo and alkyl;

or a pharmaceutically acceptable salt thereof.

2. A compound of claim 1 wherein $R^1$ is phenyl substituted with 2 substituents selected from the group consisting of halo, alkyl, and alkoxy, and is also substituted with 1 $CON(R^9)(R^{10})$ substituent; $R^2$ is halo; $R^3$ is imidazol-2-yl;

$R^4$ is phenyl that is para substituted with halo; $R^5$ is hydrogen; $R^6$ is hydrogen; $R^9$ is

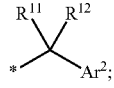

$R^{10}$ is hydrogen; $R^{11}$ and $R^{12}$ taken together is ethylene; and $Ar^2$ is pyrimidinyl; or a pharmaceutically acceptable salt thereof.

3. A compound of claim 1 wherein $R^1$ is phenyl substituted with 2 substituents selected from the group consisting of halo, alkyl, and alkoxy, and is also substituted with 1 $CON(R^9)(R^{10})$ substituent; $R^2$ is halo; $R^3$ is imidazol-2-yl; $R^4$ is phenyl that is para substituted with halo; $R^5$ is hydrogen; $R^6$ is $N(R^7)(R^8)$; $R^7$ and $R^8$ are independently hydrogen, alkyl, or alkylsulfonyl; $R^9$ is

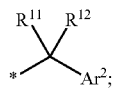

$R^{10}$ is hydrogen; $R^{11}$ and $R^{12}$ taken together is ethylene; and $Ar^2$ is pyrimidinyl; or a pharmaceutically acceptable salt thereof.

4. A compound of claim 1 where $R^6$ is hydrogen or $N(R^7)(R^8)$ and $R^7$ and $R^8$ are independently hydrogen, alkyl, or alkylsulfonyl; or a pharmaceutically acceptable salt thereof.

5. A compound of claim 1 selected from the group consisting of

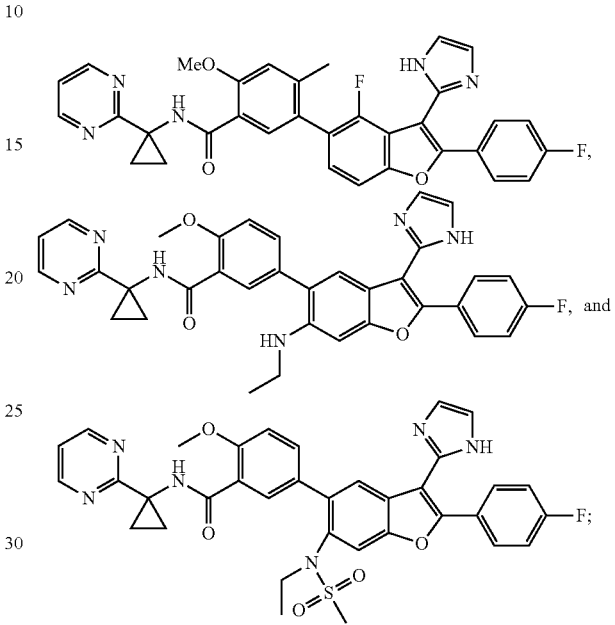

or a pharmaceutically acceptable salt thereof.

6. A composition comprising a compound of claim 1, or a pharmaceutically acceptable salt thereof, and a pharmaceutically acceptable carrier.

* * * * *